US00RE48049E

(19) United States
(12) Reissued Patent
Zachek et al.

(10) Patent Number: US RE48,049 E
(45) Date of Reissued Patent: Jun. 16, 2020

(54) PASSIVELY ACTIVATED SAFETY NEEDLE ASSEMBLIES AND METHODS OF USE

(71) Applicant: Becton, Dickinson and Company, Franklin Lakes, NJ (US)

(72) Inventors: Matthew Zachek, San Diego, CA (US); Ryan Lakin, Fredon, NJ (US)

(73) Assignee: Becton, Dickinson and Company, Franklin Lakes, NJ (US)

(21) Appl. No.: 15/814,493

(22) Filed: Nov. 16, 2017

Related U.S. Patent Documents

Reissue of:
(64) Patent No.: 9,186,466
Issued: Nov. 17, 2015
Appl. No.: 13/793,582
Filed: Mar. 11, 2013

U.S. Applications:
(63) Continuation of application No. 15/812,245, filed on Nov. 14, 2017, now Pat. No. Re. 47,472, which is an application for the reissue of Pat. No. 9,186,466.

(60) Provisional application No. 61/610,558, filed on Mar. 14, 2012.

(51) Int. Cl.
*A61M 5/00* (2006.01)
*A61M 5/32* (2006.01)

(52) U.S. Cl.
CPC ..... *A61M 5/3213* (2013.01); *A61M 5/326* (2013.01)

(58) Field of Classification Search
CPC ..... A61M 5/326; A61M 2005/3247; A61M 2005/3267; A61M 2005/325; A61M 5/3213
See application file for complete search history.

(56) References Cited

U.S. PATENT DOCUMENTS

| | | | | |
|---|---|---|---|---|
| 4,795,432 | A | 1/1989 | Karczmer | |
| 4,813,940 | A | 3/1989 | Parry | |
| 4,887,998 | A | 12/1989 | Martin et al. | |
| 4,911,706 | A | 3/1990 | Levitt | |
| 4,950,250 | A | 8/1990 | Haber | |
| 5,304,151 | A | 4/1994 | Kuracina | |
| 5,370,628 | A | 12/1994 | Allison et al. | |
| 5,395,347 | A | 3/1995 | Blecher | |
| 5,549,558 | A * | 8/1996 | Martin | 604/10 |

(Continued)

FOREIGN PATENT DOCUMENTS

| | | | |
|---|---|---|---|
| CA | 2803761 | A1 | 12/2011 |
| CN | 103079610 | A | 5/2013 |

(Continued)

OTHER PUBLICATIONS

PCT International Preliminary Report on Patentability in PCT/US2013/031214, dated Sep. 16, 2014, 6 pages.

(Continued)

*Primary Examiner* — Cary E Wehner
(74) *Attorney, Agent, or Firm* — Servilla Whitney LLC

(57) ABSTRACT

Described are passively activated safety needle assemblies and methods for use. The assemblies comprise an elongate hollow outer shield, an elongate hub slidably engaged within the outer shield and biased to move proximally with respect to the outer shield. A locking ring in the hub has a ring element that cooperates with an activation element on the outer shield rotate the locking ring and disable the assembly.

13 Claims, 16 Drawing Sheets

(56) References Cited

U.S. PATENT DOCUMENTS

| | | | | |
|---|---|---|---|---|
| 5,591,138 | A | 1/1997 | Vaillancourt | |
| 5,688,241 | A | 11/1997 | Asbaghi | |
| 5,919,168 | A | 7/1999 | Wheeler | |
| 5,964,731 | A | 10/1999 | Kovelman | |
| 5,984,899 | A | 11/1999 | D'Alessio | |
| 6,077,253 | A | 6/2000 | Cosme | |
| RE36,885 | E | 9/2000 | Blecher | |
| 6,171,284 | B1 | 1/2001 | Kao et al. | |
| 6,537,259 | B1 | 3/2003 | Niermann | |
| 6,635,032 | B2 | 10/2003 | Ward | |
| 6,695,819 | B2 | 2/2004 | Kobayashi | |
| 6,773,415 | B2 | 8/2004 | Heiniger | |
| 6,832,992 | B2 | 12/2004 | Wilkinson | |
| 6,855,130 | B2 | 2/2005 | Saulenas et al. | |
| 6,884,237 | B2 | 4/2005 | Asbaghi | |
| 6,926,697 | B2 | 8/2005 | Malenchek | |
| 6,986,760 | B2 | 1/2006 | Giambattista et al. | |
| 7,101,351 | B2 | 9/2006 | Crawford et al. | |
| 7,118,552 | B2 | 10/2006 | Shaw et al. | |
| 7,344,517 | B2 | 3/2008 | Schiller | |
| 7,357,783 | B2 | 4/2008 | Millerd | |
| 7,361,159 | B2 | 4/2008 | Fiser et al. | |
| 7,390,312 | B2 | 6/2008 | Barrelle | |
| 7,462,168 | B2 | 12/2008 | Stonehouse et al. | |
| 7,468,054 | B2 | 12/2008 | Crawford et al. | |
| 7,513,888 | B2 | 4/2009 | Sircom | |
| 7,553,293 | B2 | 6/2009 | Jensen et al. | A61M 5/326 604/110 |
| 7,604,613 | B2 | 10/2009 | Crawford et al. | |
| 7,811,261 | B2 | 10/2010 | Rubinstein | |
| 8,062,265 | B2 | 11/2011 | Millerd | |
| 8,162,882 | B2 | 4/2012 | Rubinstein | |
| 8,162,883 | B2 | 4/2012 | Takemoto | |
| 8,246,599 | B2 | 8/2012 | Millerd | |
| 8,303,541 | B2 | 11/2012 | Chun | |
| 8,333,738 | B2 | 12/2012 | Millerd | |
| 8,439,870 | B2 | 5/2013 | Moyer | |
| 8,496,627 | B2 | 7/2013 | Chelak | |
| 8,636,688 | B2 | 1/2014 | Shaw | |
| 8,636,703 | B2 | 1/2014 | Foshee | |
| 8,647,307 | B2 | 2/2014 | Gratwohl | |
| 8,663,129 | B2 | 3/2014 | Allen | |
| 8,747,355 | B2 | 6/2014 | Rubinstein | |
| 8,827,961 | B2 | 9/2014 | Emmott | |
| 8,968,241 | B2 | 3/2015 | Liversidge | |
| 8,979,794 | B2 | 3/2015 | Chevallier | |
| 9,050,416 | B2 | 6/2015 | Feret | |
| 9,061,106 | B2 | 6/2015 | Roberts | |
| 9,067,024 | B2 | 6/2015 | Roberts | |
| 9,186,466 | B2 | 11/2015 | Zachek | |
| 9,352,099 | B2 | 5/2016 | Roberts | |
| 9,352,100 | B2 | 5/2016 | Ward | |
| 9,352,101 | B2 | 5/2016 | Roberts | |
| 9,370,327 | B2 | 6/2016 | Teoh | |
| 9,408,632 | B2 | 8/2016 | Erskine | |
| 9,445,760 | B2 | 9/2016 | Allen | |
| 9,694,140 | B2 | 7/2017 | Rubinstein | |
| 9,848,810 | B2 | 12/2017 | Allen | |
| 2003/0060776 | A1* | 3/2003 | Heiniger | A61M 5/326 604/198 |
| 2005/0059936 | A1 | 3/2005 | Fiser et al. | |
| 2005/0119627 | A1 | 6/2005 | Crawford | |
| 2006/0211985 | A1 | 9/2006 | Wang | |
| 2008/0215001 | A1* | 9/2008 | Cowe | 604/110 |
| 2009/0012478 | A1 | 1/2009 | Weston | |
| 2009/0281492 | A1 | 11/2009 | Millerd | |
| 2010/0274199 | A1 | 10/2010 | Weston | |
| 2010/0298770 | A1 | 11/2010 | Rubinstein | |
| 2011/0077592 | A1 | 3/2011 | Takemoto | |
| 2011/0288491 | A1* | 11/2011 | Newman | A61M 5/326 604/198 |
| 2013/0046246 | A1* | 2/2013 | Cross | A61M 5/326 604/189 |
| 2013/0110051 | A1* | 5/2013 | Ruan | 604/198 |
| 2014/0036483 | A1 | 2/2014 | Chen | |
| 2014/0135706 | A1 | 5/2014 | Rubinstein | |
| 2014/0228772 | A1 | 8/2014 | Ward | |
| 2015/0094659 | A1 | 4/2015 | Schraga | |
| 2015/0182704 | A1 | 7/2015 | Chevallier | |
| 2015/0190580 | A1 | 7/2015 | Imai | |
| 2015/0190586 | A1 | 7/2015 | Takemoto | |

FOREIGN PATENT DOCUMENTS

| | | | |
|---|---|---|---|
| DE | 10009814 | | 9/2001 |
| EP | 2585146 | B1 | 3/2017 |
| JP | 2013529973 | A | 7/2013 |
| MX | 2013000081 | A | 3/2013 |
| MX | 349289 | B | 7/2017 |
| WO | WO-2008/050518 | | 5/2008 |
| WO | WO2009114777 | * | 9/2009 |
| WO | WO-2011/149455 | | 12/2011 |
| WO | 2012013587 | A1 | 2/2012 |

OTHER PUBLICATIONS

PCT International Search Report in PCT/US2013/031214, dated May 24, 2013, 3 pages.

PCT International Written Opinion in PCT/US2013/031214, dated May 24, 2013, 5 pages.

* cited by examiner

PASSIVELY ACTIVATED SAFETY NEEDLE ASSEMBLIES AND METHODS OF USE

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

CROSS-REFERENCE TO RELATED APPLICATIONS

[This application claims priority under 35 U.S.C. §119(e) to] *Notice: More than one reissue application has been filed for the reissue of U.S. Pat. No. 9,186,466. The reissue applications are application Ser. No. 15/814,493 (the present application), which is an application for reissue of U.S. Pat. No. 9,186,466 and a continuation of reissue application Ser. No. 15/812,245, which is also an application for reissue of U.S. Pat. No. 9,186,466. U.S. Pat. No. 9,186,466 claims the benefit of* U.S. Provisional Application No. 61/610,558, filed Mar. 14, 2012, the [disclosures] *disclosure* of which [are] *is* incorporated herein by reference in their entirety.

TECHNICAL FIELD

The subject invention relates generally to a passively activated safety needle assemblies and methods for use. The assemblies comprise an elongate hollow outer shield, an elongate hub slidably engaged within the outer shield and biased to move proximally with respect to the outer shield.

BACKGROUND

Embodiments of the invention generally relate to passively activated safety needle assemblies. More specifically, embodiments of the invention are directed to passively activated safety needle assemblies comprising a locking ring and outer shield with cooperative structures to disable the needle assemblies in a user safe manner.

Needle devices are used throughout the medical industry for the injection and withdrawal of a wide variety of fluids and solutions into and from the human body. Because of the numerous potential hazards associated with the handling and manipulation of bodily fluids, and particularly blood, there are a number of known safety features that are frequently incorporated into various types of needle devices to protect the practitioner from accidental exposure to the needle.

Prior safety needle devices having a retractable sheath require multi-component retraction and locking elements and often do not incorporate reuse prevention features. Therefore, the retraction mechanism may be reset so the syringe barrel may be reused. The reuse of syringe assemblies without sterilization or sufficient sterilization is believed to facilitate the transfer of contagious diseases. Further, the retraction features of conventional syringes also often require the user to actively activate the retraction mechanism. Accordingly, the chance of human error in failure to activate or properly activate the retraction mechanism can lead to continued exposure of needles Prior retracting sheath safety needle devices have been developed to include a single-use cover assembly that obscures a substantial majority or an entirety of an injection needle from view before, during, and after an injection procedure. However, many injection procedures require that the practitioner see the needle and injection site or know precisely the depth to which the needle is inserted in the patient's tissue to be sure that medication is delivered to an appropriate location.

There is an ongoing need in the art for needles which passively activate a safety mechanism to prevent injury to the healthcare worker, or others, and provide improved visibility of the needle.

SUMMARY

One or more embodiments of the invention are directed to passively activated safety needle assemblies. The assemblies comprise an outer shield, a hub and a locking ring. The outer shield is an elongate, hollow outer shield having a distal end, a proximal end, an outer surface and an inner surface. The outer shield includes an activation element protruding inwardly from the inner surface. The outer shield also includes at least one finger biased radially inwardly. The hub is an elongate hub having a distal end and a proximal end. The hub is slidably engaged with the outer shield and biased to move in a proximal direction. The hub includes a longitudinal groove that guides the activation element during relative sliding motion between the hub and the outer shield. The locking ring is on the hub and has a ring element complementary to the activation element and at least one ramped surface radially spaced from the ring element. The ramped surface providing a proximal facing edge. Wherein, distal movement of the outer shield with respect to the hub causes the activation element and ring element to rotate the locking ring such that the at least one finger aligns with the ramped surface. Subsequent proximal movement of the outer shield causes the at least one finger to engage the proximal facing edge, preventing further relative movement of the outer shield and hub.

In some embodiments, the hub includes a circumferential channel and the locking ring is rotatably seated within the circumferential channel.

In one or more embodiments, the ring element is a substantially triangular wedge with a proximal end and a distal end, the proximal end being narrower than the distal end. In some embodiments, the activation element is a substantially triangular wedge with a proximal end and distal end, the proximal end being wider than the distal end. In one or more embodiments, the activation element is a substantially triangular wedge with a proximal end and distal end narrower than the proximal end and the ring element if a complementary triangular wedge with a proximal end and distal end wider than the proximal end.

In some embodiments, there are two activation elements. In one or more embodiments, the activation elements are positioned on opposite sides of the outer shield.

In some embodiments, there are two ring elements. In one or more embodiments, the ring elements are on opposite sides of the locking ring.

In some embodiments, the locking ring further comprises a projection extending one or more of proximally and distally from the locking ring. In one or more embodiments, the elongate hub further comprises at least one complementary recess that engages the projection.

In some embodiments, the locking ring further comprises a longitudinal opening.

One or more embodiments further comprise a spring element positioned within the elongate, hollow outer shield adjacent the proximal end of the elongate hub. In some embodiments, the elongate, hollow outer shield further comprises an aperture that permits a needle to extend therethrough. Some embodiments further comprise a needle extending from the proximal end of the elongate hub within the spring element and the outer shield such that proximal movement of the hub with respect to the outer shield compresses the spring element and causes the needle to project through the aperture. In some embodiments, the elongate hub further comprises a Luer connector on the distal end.

One or more embodiments further comprise a needle positioned within the hub so that distal movement of the outer shield with respect to the hub compresses the spring element and causes the needle to extend from the distal end of the hub. In some embodiments, the outer shield further comprises a Luer connector on the proximal end.

Additional embodiments of the invention are directed to passively activated safety needle assemblies comprising a hub, a locking ring, an outer shield, a spring element and a needle. The hub has an elongate cylindrical body with an outer surface, an inner surface, a distal end and a proximal end defining a length, an aperture extending through the length of the hub, at least two longitudinal grooves extending at least partially along the length of the hub and a circumferential channel. The locking ring has a cylindrical body rotatably positioned in the circumferential channel of the hub and coaxial with the hub. The locking ring includes at least one ring element extending outwardly from an outside surface of the locking ring. The at least one ring element has a proximal end, a distal end and a ramped face extending from the proximal end to the distal end. The locking ring has at least one ramp-shaped locking tab extending outwardly from the outside surface of the ring. The at least one locking tab has a proximal locking face extending from the outside surface of the cylindrical body. The outer shield is coaxial to and slidable around the hub and locking ring. The outer shield includes an elongate hollow cylindrical body with an open distal end and a closed proximal end with an aperture to permit a needle to move therethrough. The out shield includes at least one activation element projecting inwardly from an interior surface of the outer shield that engages the at least one ring element. The at least one activation element is sized to slidably move within a longitudinal groove on the hub and has a shape that cooperatively interacts with the at least one ring element on the locking ring. The outer shield also has at least one finger projecting inwardly and sized to slidably move within a longitudinal groove on the hub. The spring element is positioned adjacent the proximal end of the hub within the outer shield. The needle extends from the proximal end of the hub within the outer shield and the spring element. Wherein proximally directed force on the hub causes compression of the spring element, extends a tip of the needle through the aperture in the outer shield and causes the activation element to exert distally directed force onto the ring element to rotate the locking ring such that the at least one finger on the outer shield aligns with the at least one ramped surface.

In some embodiments, subsequent release of the proximally directed force allows the spring element to expand causing distal movement of the hub with respect to the outer shield so that the at least one finger slides over the at least one ramped surface and that additional proximal movement of the hub is prevented by interaction of the at least one finger with the proximal locking face.

DETAILED DESCRIPTION

Figure 1:
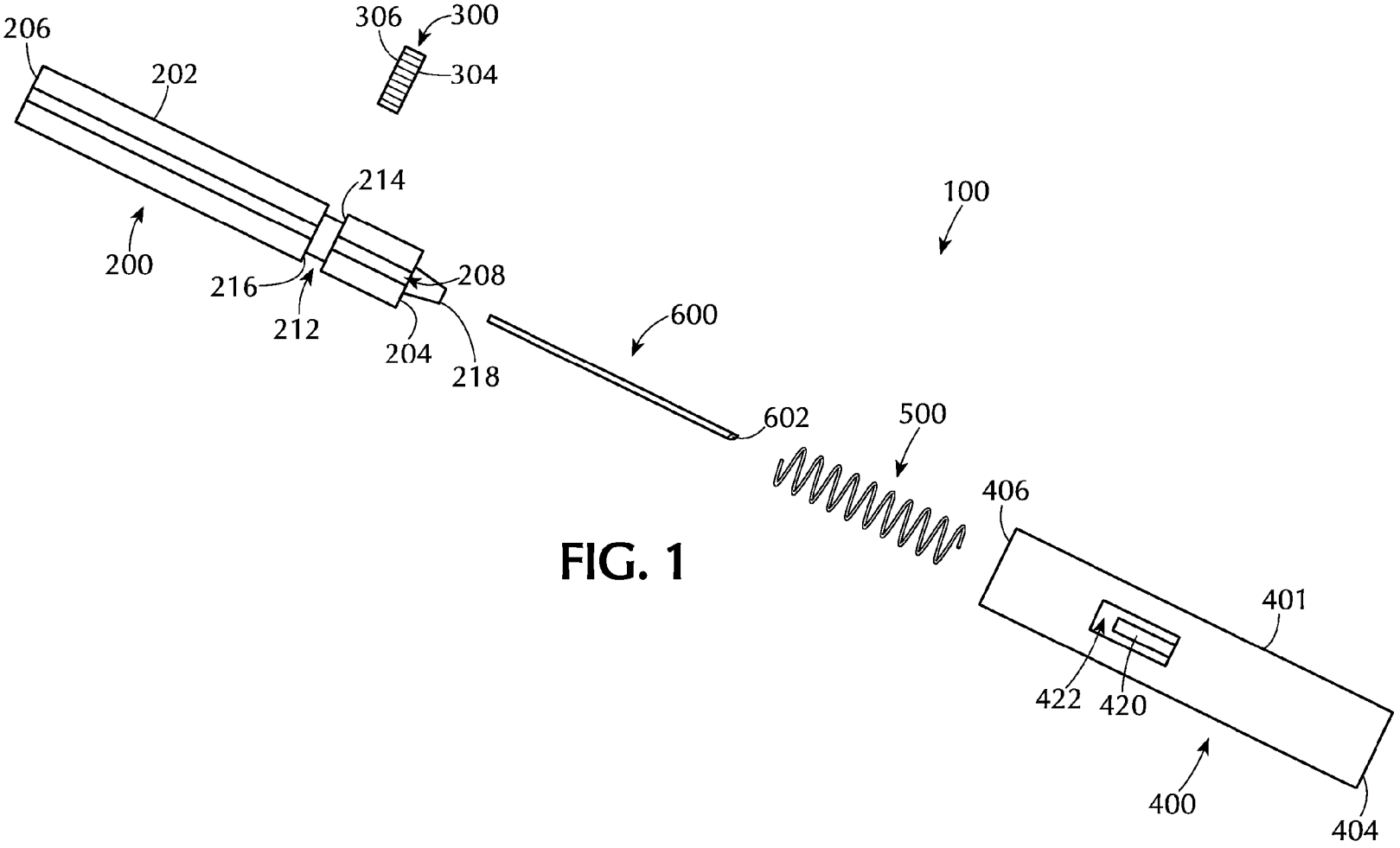
FIG. 1 is an exploded view of a safety needle device in accordance with one or more embodiments of the invention.

Before describing several exemplary embodiments of the invention, it is to be understood that the invention is not limited to the details of construction or process steps set forth in the following description. The invention is capable of other embodiments and of being practiced or being carried out in various ways.

Embodiments of the invention comprise a design for a safety hypodermic needle that allows health care workers to passively activate a safety mechanism during administration of hypodermic injections. As the healthcare worker administers an injection using the described needles, a shield surrounding the needle is allowed to travel freely against the injection site. As the needle is withdrawn from the patient, the shield will retract over the needle (supported by a material containing spring like material properties) and lock into place, providing protection against needle stick injuries. This locking feature also prohibits the re-use of the product for patient safety.

Embodiments of the device implement a ring-based component that tracks along a needle hub to provide the dual states (i.e., locking and non-locking) of the device.

Embodiments of the invention described are completely passive, needle-based, safety device. That is, that no extra action is required by the healthcare worker to activate the safety mechanism. Needle-based safety does not require a specialty syringe to activate the safety mechanism, allowing the device to be used on any standard Luer syringe. This benefit allows for higher adoption rates (as it can be applied in more situations), lower cost (no specialty syringe), and greater affordability. Passive safety may be seen as a benefit regarding the prevention of needle stick injuries. An additional benefit of the rotating ring design, embodiments of the invention do not require the protective shield to rotate to activate the safety mechanism (as this might not always be possible, and thus prevent the activation of the safety mechanism).

As described further below, some embodiments of the invention in the "inactivated" state comprise a standard Luer connecting hub and needle assembly, a clear outer shield, a snap-on ring and a spring element. Alternate embodiments of the invention include the reversal of these components; meaning, that the outer shield may contain the Luer connection while the inner shield may serve as the injection site. A device in the "inactive" or "locked" state can be observed by the position of the rotating ring. The rotating ring in some embodiments is a snap-on feature with an opening at one end. The ring can either be friction fit, preventing movement, or could contain one or more locking features to prevent premature movement of the ring prior to activation. In addition, though a 4-channel rotating ring design is shown in many of the drawings, multiple rings (or an alternate ring) can also be implemented to achieve similar results.

The function of the safety mechanism is described with reference to the Figures below. Briefly, during the administration of medication, an activation element on the outer shield mechanically forces the movement of a complimentary element on the rotating ring. Prior to the activation, locking fingers are allowed to proceed unabated in the axial direction. After injection is complete, the spring element forces the axial movement of the outer shield to its original position. The spring element also contains enough energy to propel the locking finger over the uniquely shaped feature on the locking ring, which serves to allow the locking finger to pass over them but prevent their return. At this point, the injection has been given and the device is considered in the "locked" state.

Figure 2:
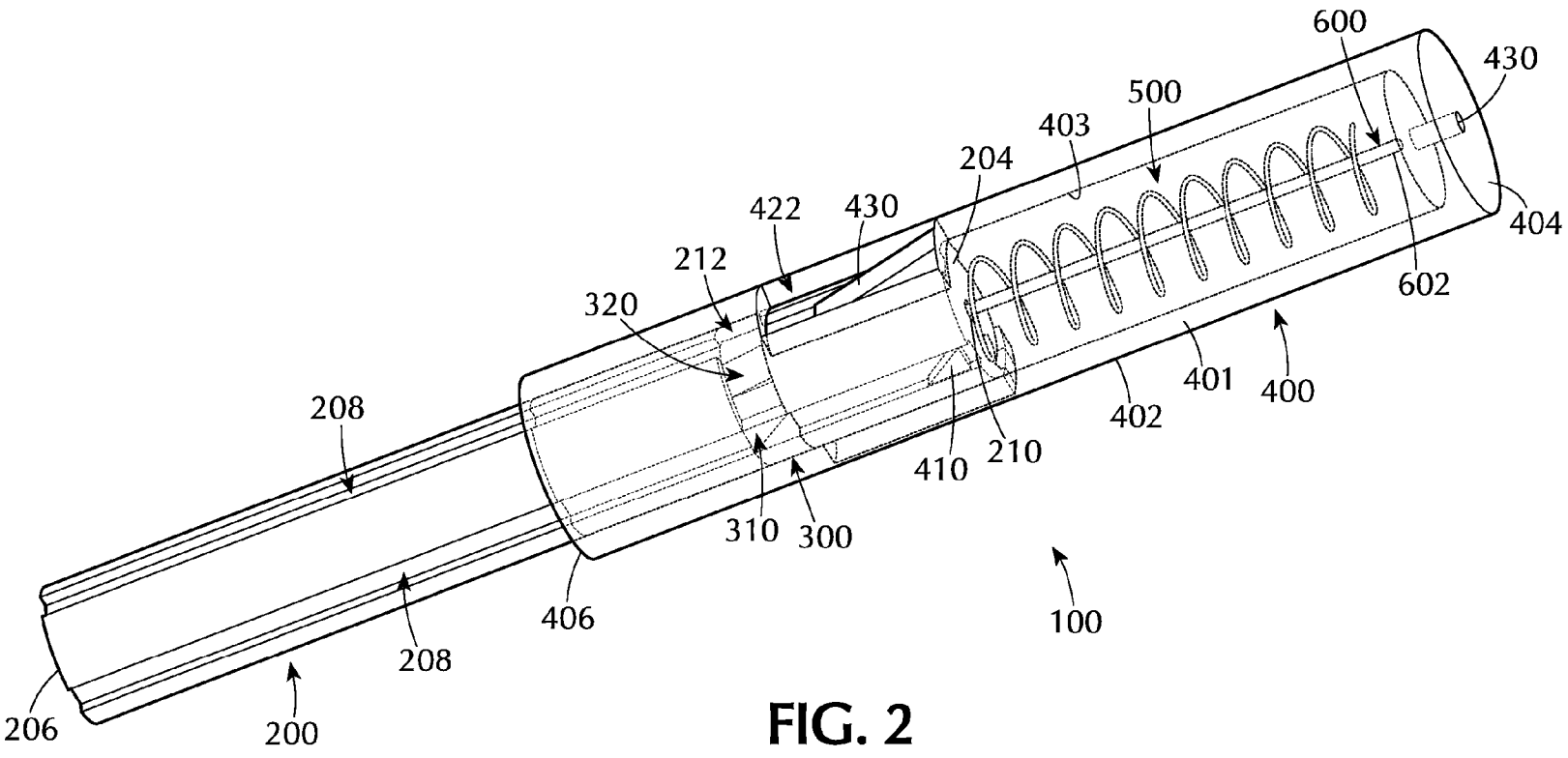
FIG. 2 is a perspective view of a safety needle device with a transparent outer shield in accordance with one or more embodiments of the invention.
Figure 3:
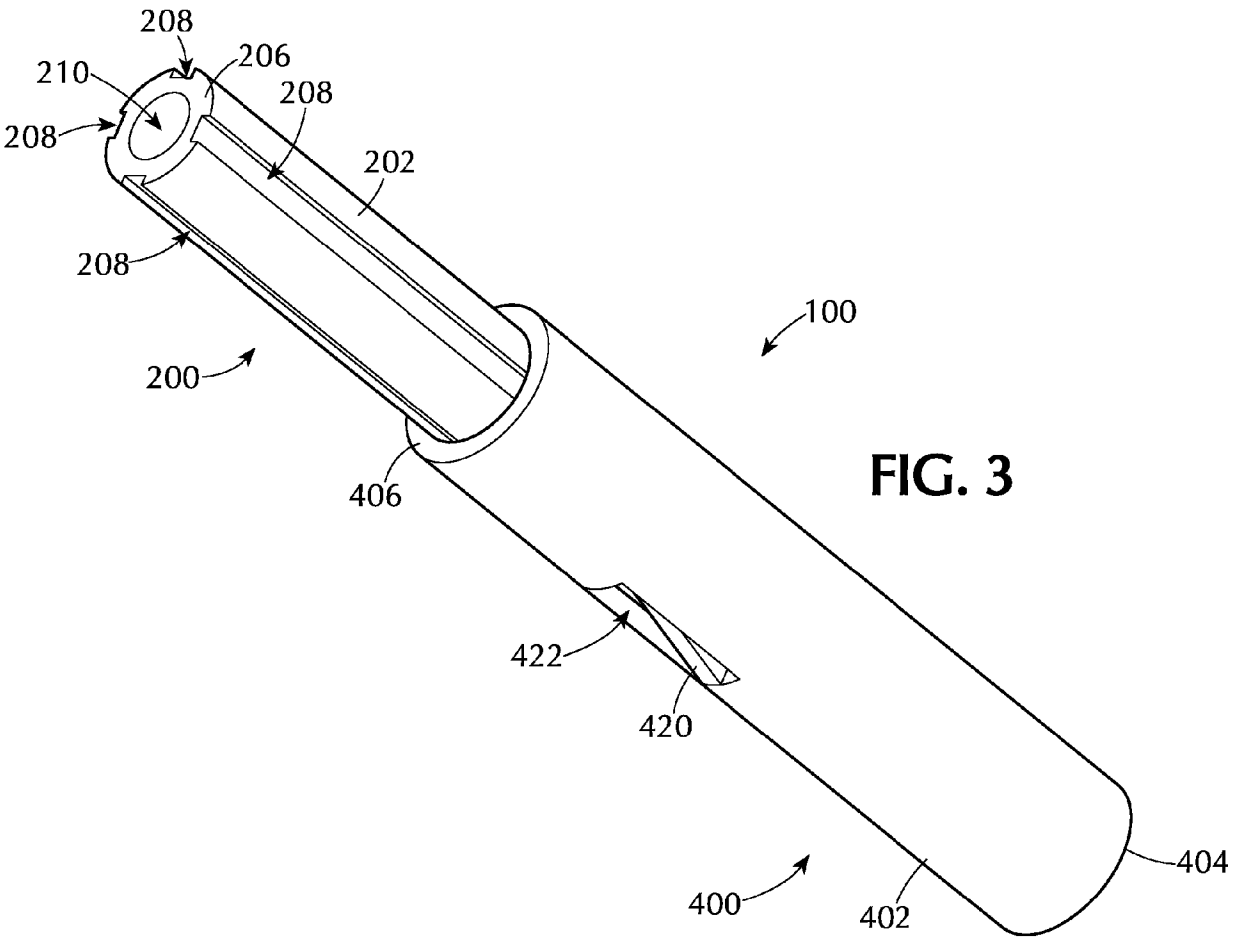
FIG. 3 is a perspective view of a safety needle device with an opaque outer shield in accordance with one or more embodiments of the invention.

FIGS. 1-3 show an embodiment of a passively activate safety needle assembly 100 in accordance with some aspects of the invention. The assembly 100 comprises a hub 200, a locking ring 300 and an outer shield 400. A spring element 500 and a needle element 600. FIG. 1 shows an exploded view of an embodiment of one or more embodiments of the invention. FIG. 2 shows a view of the needle assembly of FIG. 1 in an assembled state with a transparent outer shield 400. FIG. 3 shows another view of the needle assembly of FIG. 1 in an assembled state from a reverse angle to that of FIG. 2 with an opaque outer shield 400. For ease of describing the various features, aspects and embodiments, a common numbering system is used throughout so similar features have similar numbers between Figures.

Figure 4:
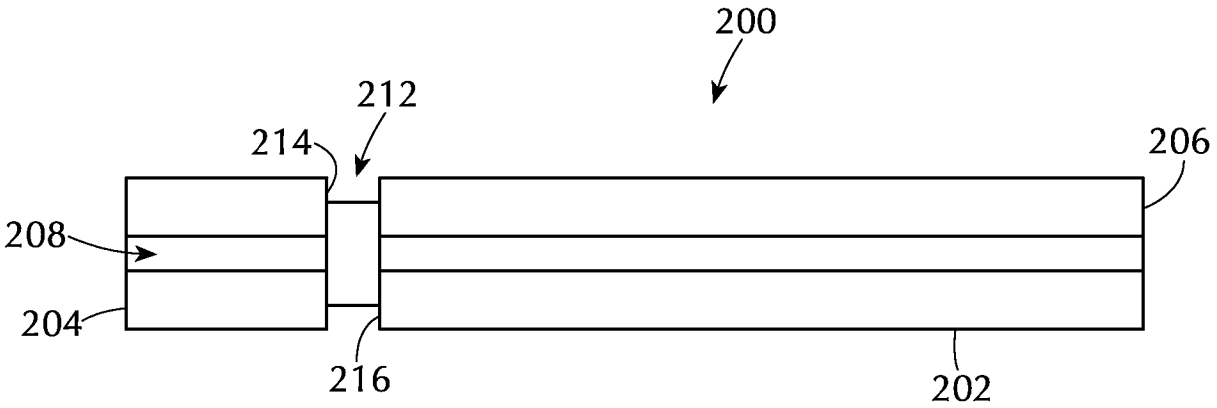
FIG. 4 is a side view of a hub portion of a safety needle device in accordance with one or more embodiments of the invention.
Figure 5:
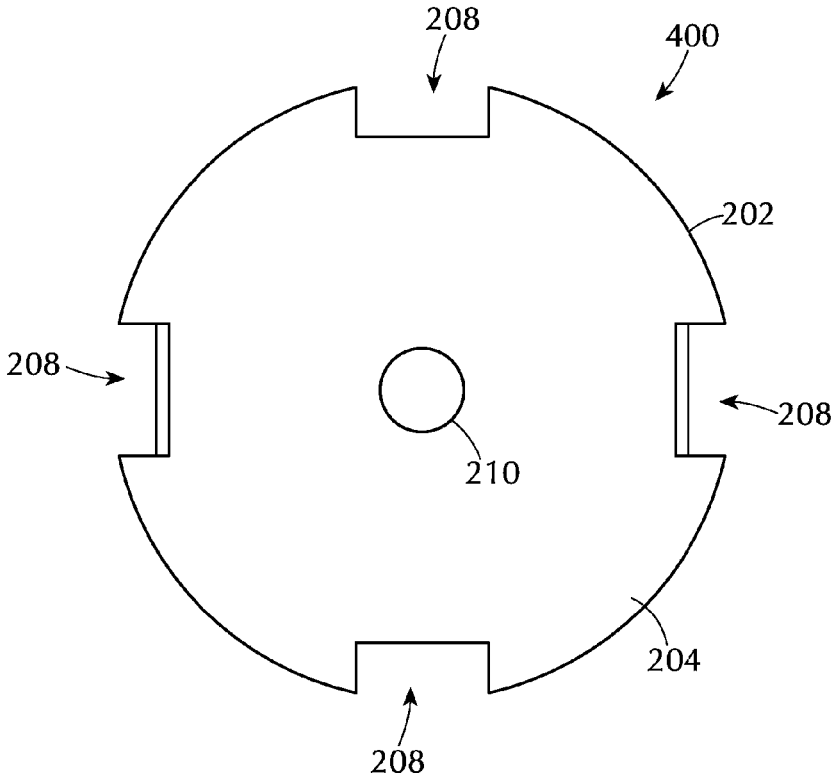
FIG. 5 is an end view of a hub portion of a safety needle device in accordance with one or more embodiments of the invention.

With reference to FIGS. 4 and 5, the hub 200 of one or more embodiments, comprises an elongate body 202 with a proximal end 204 and a distal end 206 defining an overall length. FIG. 4 shows a side view of the hub 200 and FIG. 5 shows an end view of the hub 200 looking at the distal end 206. As will be described further below, the hub 200 is slidably engaged with the outer shield 400 and the hub 200 is biased to move in a proximal direction relative to the outer shield 400.

The hub 200 of some embodiments includes at least one longitudinal groove 208 which can be used to engage and guide one or more elements on the outer shield 400 during relative sliding motion between the hub and the outer shield, as will be described further. In FIG. 4, one longitudinal groove is shown which can engage and guide one element from the outer shield. FIG. 5 shows an end view in which there are four longitudinal grooves 208 visible. Any or all of these longitudinal grooves 208 can be used to guide elements from the outer shield 400. While hubs with one and four longitudinal grooves have been shown, it will be understood by those skilled in the art that there can be any suitable number of grooves depending on the number of elements from the outer shield, or other components, which need to be guided. As will be understood by those skilled in the art, guiding an element means that the element moves within the longitudinal groove and is substantially prevented from twisting circumferentially about the hub 200.

The shape of the hub 200 can be varied depending on the desired shape of, for example, the outer shield 400. Here, the hub 200 is shown having a roughly cylindrical shape which may be useful for engaging a roughly cylindrical outer shield. In some embodiments, the hub is an elongate triangle (e.g., triangular prism), elongate tetrahedron, elongate pentahedron, elongate hexahedron, elongate heptahedron, elongate octahedron, elongate nonahedron, elongate decahedron, etc. The shape of the outer shield 400 in some embodiments, substantially conforms to the shape of the hub 200. For example, if the hub 200 is generally an elongate octahedron, then the outer shield 400 would also be an elongate octahedron roughly concentric to the hub 200. As used in this specification and the appended claims, the term "roughly cylindrical" means that the shape is a cylinder with grooves or channels as that shown in FIG. 5.

The hub 200 of some embodiments has a circumferential channel 212 extending about the circumference of the elongate body 202. The channel 212 can be positioned anywhere along the length of the elongate body 202. As shown in the Figures, the channel 212 is positioned nearer to the proximal end 204 than the distal end 206. This is merely one possible configuration and should not be taken as limiting the scope of the invention. In some embodiments, the circumferential channel 212 is nearer to the distal end 206 than the proximal end 204. In some embodiments, the channel 212 is immediately adjacent one of the proximal end 204 and distal end 206. In embodiments like that shown in FIG. 4, the circumferential channel 212 has a proximal end 214 and a distal end 216. The distance between the proximal end 214 and distal end 216, which can also be referred to as the length of the circumferential channel 212, can be any size as required. In some embodiments, the circumferential channel 212 is about the same length as the locking ring 300 so that the locking ring is friction fit within the channel 212 as described further below.

Figure 6:
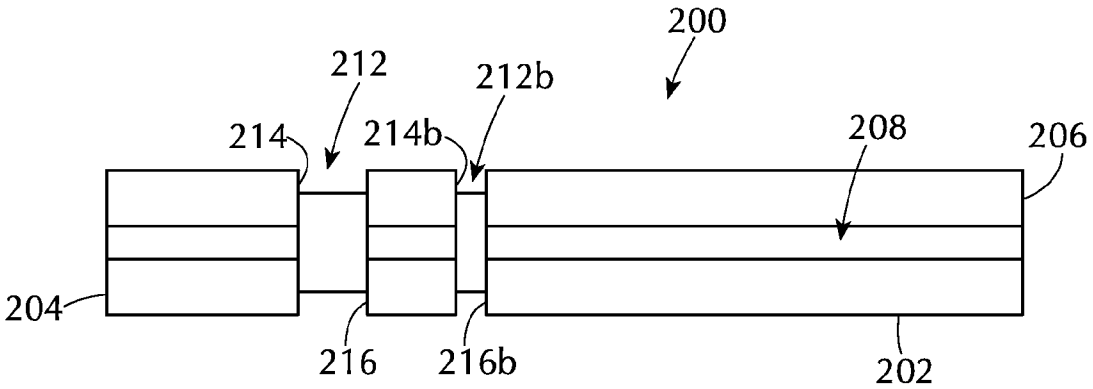
FIG. 6 is a side view of a hub portion of a safety needle device in accordance with one or more embodiments of the invention.

The hub 200 shown in FIG. 4 has a single circumferential channel 212. This is merely illustrative and should not be taken as limiting the scope of the invention. In some embodiments, as shown in FIG. 6, the hub 200 includes two or more circumferential channels 212, 212b. Any or all of the channels can be used in conjunction with one or more locking rings and each of the channels can be the same length or different lengths. The first channel 212 is closer to the proximal end 204 of the elongate body 202 and has a proximal end 214 and distal end 216, the difference between defining a first channel length. The second channel 212b is closer to the distal end 206 of the elongate body 202 and has a proximal end 214b and a distal end 216, the difference between defining a second channel length. In the embodiment shown, the first channel length and the second channel lengths are different.

The hub 200 also includes an aperture 210 extending through the length of the elongate body 202. The aperture 210 extends along the length of the elongate body from the distal end to the proximal end so that a fluid, needle, or other component can pass through the elongate body 202.

Figure 7:
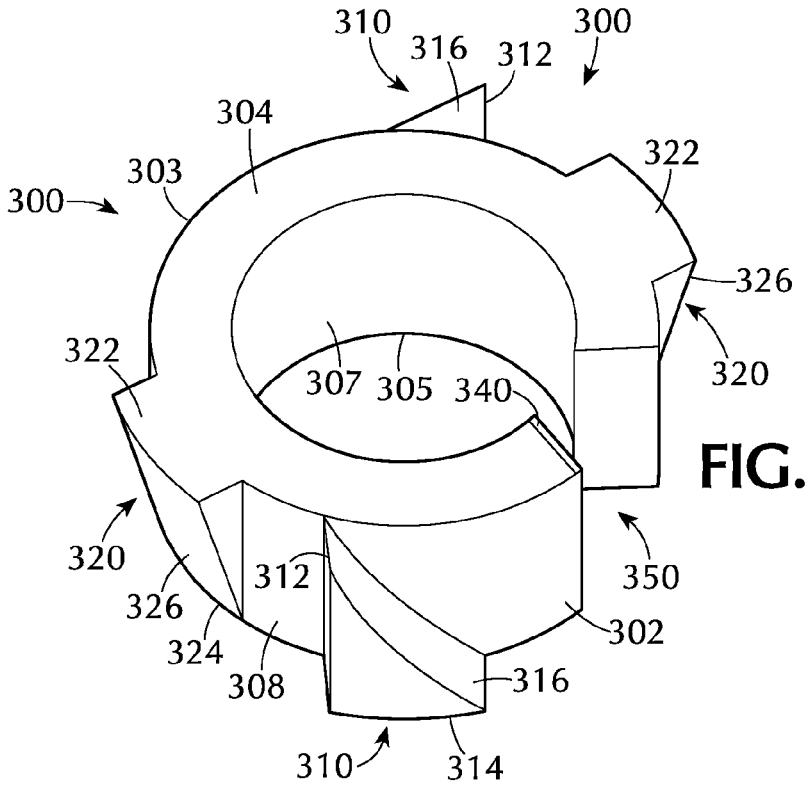
FIG. 7 is an isometric view of a locking ring in accordance with one or more embodiments of the invention.
Figure 8:
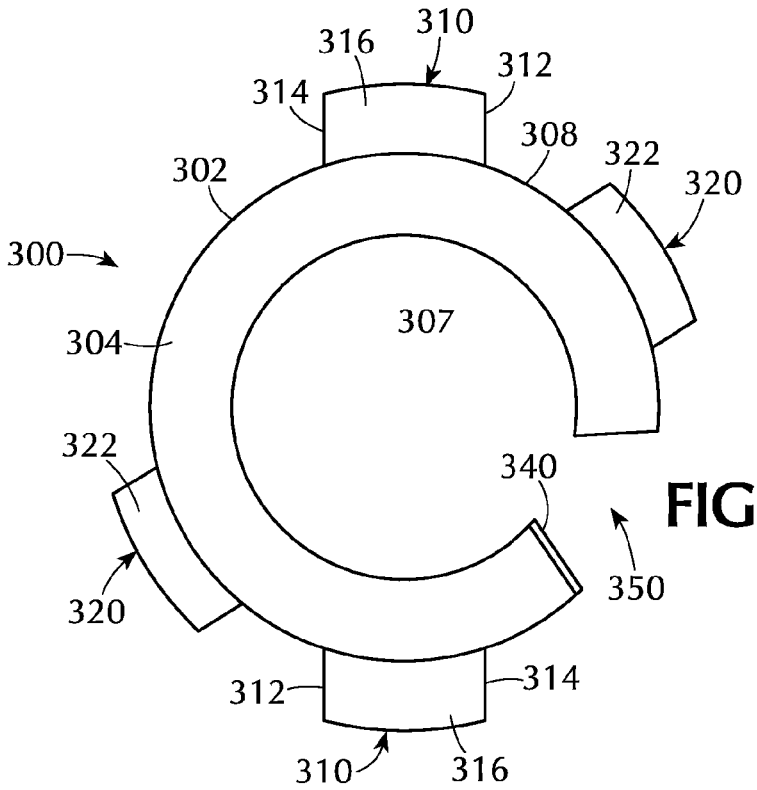
FIG. 8 is a top view of the locking ring of a safety needle device of FIG. 7 in accordance with one or more embodiments of the invention.

FIGS. 7-8 show a locking ring 300 in accordance with one or more embodiments of the invention. The locking ring 300 includes a hollow cylindrical body 302 having a proximal end 303 with a proximal face 304 and a distal end 305 and distal face 306 defining a locking ring length extending along an axis. The hollow cylindrical body 302 has an inside surface 307 and an outside surface 308.

The locking ring 300 is generally sized to fit within the at least one circumferential channel 212 in the hub 200 so that the proximal face 304 is adjacent the proximal end 214 of the channel 212 and the distal face is adjacent the distal end 216 of the channel 212 in the hub 200. The locking ring 300 can be sized to be rotatably seated within the circumferential channel 212 of the hub. As used in this specification and the appended claims, the term "rotatably seated" means that the locking ring can rotate within the channel so that the locking ring and the hub remain substantially concentric.

The locking ring 300 includes at least one ring element 310 which extends outwardly from the outside surface 308 of the hollow cylindrical body 302. The at least one ring element 310 is used, in conjunction with an activation element on the outer shield, to rotate the locking ring 300 within the circumferential channel 212 of the hub. The shape of the ring element 310 works cooperatively with the shape of the activation element. It will be understood by those skilled in the art that the shapes shown for the ring element and activation element are merely exemplary and that other shapes can also be employed. Suitable shapes include those in which a distally directed force exerts a rotational force on the locking ring.

In the embodiments shown in FIGS. 7-8, the at least one ring element 310 has a proximal end 312 and a distal end 314. A ramped face 316 extends from the proximal end 312 to the distal end 214 of the ring element 310. The ramped face 316 of some embodiments has an axis that is offset from the axis of the hollow cylindrical body 302. In one or more embodiment, distally directed force on the ramped face 316 provides an axially directed force to rotate the locking ring within the circumferential channel 212.

The ring element 310 shown in FIGS. 7-8 is wedge shaped. Stated differently, the ring element 310 shown is substantially triangular with a proximal end 312 being narrower than the distal end 314. The proximal end 312 of the ring element 310 is about even with the proximal face 304 of the hollow cylindrical body 302 and the distal end 314 of the ring element 310 is about even with the distal face 306 of the hollow cylindrical body 302. It will be understood by those skilled in the art that the proximal end 312 of the ring element 310 does not need to be even with the proximal face 314 and that the distal end 314 of the ring element 310 does not need to be even with the distal face 316 of the ring element 310.

Figure 9:
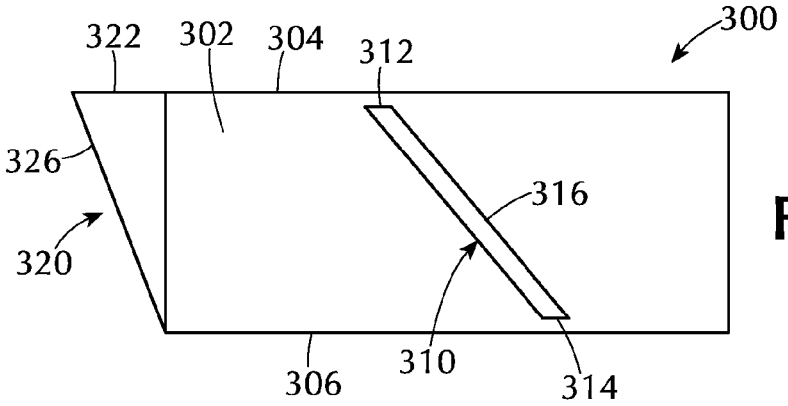
FIG. 9 is a side view of a locking ring of a safety needle device in accordance with one or more embodiments of the invention.
Figure 10:
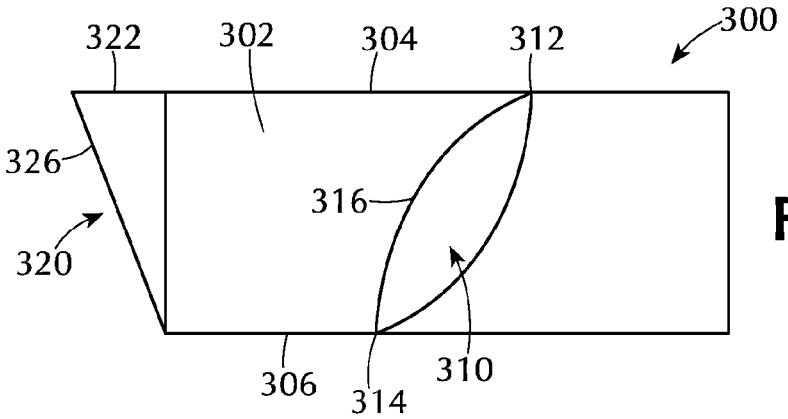
FIG. 10 is a side view of a locking ring of a safety needle device in accordance with one or more embodiments of the invention.
Figure 11:
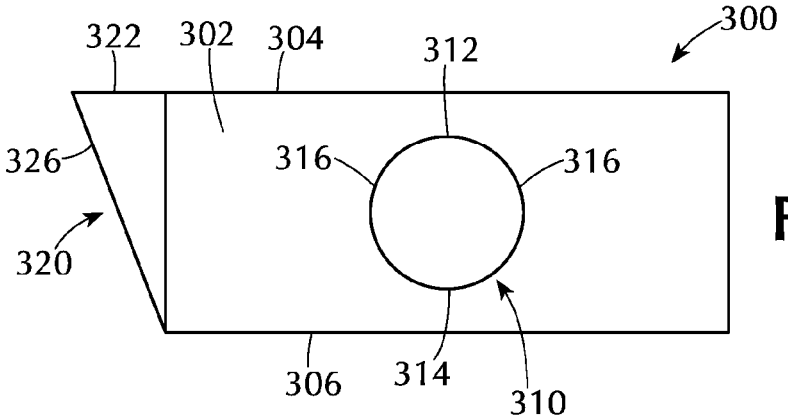
FIG. 11 is a side view of a locking ring of a safety needle device in accordance with one or more embodiments of the invention.

FIGS. 9-11 show additional embodiments of the locking ring 300 with different shaped ring elements 310. FIG. 9 shows a ring element 310 that is shaped like a beam that has an axis offset from the axis of the hollow cylindrical body 302 of the locking ring 300. The ring element 310 of this embodiment, has a proximal end 312 that is not even with the proximal face 304 of the hollow cylindrical body 302 and a distal end 314 that is not even with the distal face 306 of the hollow cylindrical body 302. It can be seen from the shape of the ring element 310, that a distally directed force would exert a rotational force causing the locking ring 300 to be rotated toward the left side of the Figure.

FIG. 10 shows another embodiment of a locking ring 300 in which the ring element 310 is football shaped. The ring element 310 here has a proximal end 312 even with the proximal face 304 and a distal end 314 even with the distal face 306 of the hollow cylindrical body 302. It can be seen from the shape of this ring element 10, that a distally directed force would exert a rotational force causing the locking ring 300 to be rotated toward the right side of the Figure. It will also be understood by those skilled in the art that the magnitude of the rotational force transferred from the distally directed force will vary depending on where along the ramped surface 316 the force is applied. Distally directed force at a steeper sloped region of the ramped surface 316 would exert more rotational force than force directed a shallower sloped region.

FIG. 11 shows another embodiment of a locking ring 300 in which the ring element 310 is peg-shaped. Here, the ring element 310 has a proximal end 312 which is the proximal-most point of the peg and a distal end 314 which is the distal-most point of the peg. The peg-shaped ring element 310 has more than one ramped surface 316 that can be used to transfer distally directed force into rotational force. In embodiments of this sort, the shape of the cooperating activation element on the outer shield will impact the direction of rotation of the locking ring 300.

The number of ring elements 310 can vary depending on, for example, the shape of the hub 200 and outer shield 400. At least one ring element 310 is included on the locking ring 300. The embodiment shown in FIGS. 7 and 8 have two ring elements 310, but it will be understood by those skilled in the art that any number of ring elements can be incorporated into the locking ring. For example, if the hub 200 is an elongate decahedron with ten longitudinal channels 208, then the locking ring 300 can have up to ten ring elements 310, with each of the ring elements 310 aligned with a longitudinal groove 208 on the huh 200. The alignment of the ring elements 310 with the longitudinal grooves 208 will be described in further detail below. In some embodiments, the locking ring 300 includes two ring elements 310 positioned on opposite sides of the hollow cylindrical body 302. The spacing of the ring elements 310 about the hollow cylindrical 302 can be distributed in any suitable manner and at any suitable degrees about the locking ring 300. For example, there can be two ring elements 310 spaced 180° apart, or spaced in the range of about 10° to about 170° apart. In another example there are in the range of two ring elements to 10 ring elements spaced in the range of about 5° to about 175° apart.

Referring back to FIGS. 7 and 8, the locking ring 300 also includes at least one locking tab 320 extending outwardly from the outside surface 308 of the hollow cylindrical body 302. The locking tab 320 includes a proximal locking face 322 extending a first distance from the outside surface 308 of the hollow cylindrical body 302. The locking tab 320 also includes a distal edge 324 extends a second distance from the outside surface 308 of the hollow cylindrical body 302. The second distance is less than the first distance so that a ramped face 326 extends along the length of the hollow cylindrical body 302 from the proximal locking face to the distal edge.

The first distance that the proximal locking face 322 extends from the outside surface 308 of the hollow cylindrical body 302 can be any suitable distance. In some embodiments, the proximal locking face 322 extends in the range of about 0.1 mm to about 10 mm from the outside surface 308. The proximal locking face 322 can be even with the proximal face 304 of the locking ring 300 or a distance down the outside surface 308 from the proximal face 304 so that the proximal locking face 322 is not even with the proximal face 304.

The second distance that the distal edge 324 of the locking tab 320 extends from the outside surface 308 of the hollow cylindrical body 302 can vary depending on the desired shape of the locking tab 320. The second distance is in the range of about 0 mm to about 9.9 mm and is less than first distance. In some embodiments, the second distance is substantially zero. As used in this specification and the appended claims, the term "substantially zero" means that distal edge 324 is close to being even with the outside surface 308 of the locking ring 300 and can be, for example, within the range of about 0.1 mm beneath the outside surface 308 and about 0.1 mm above the outside surface 308 of the locking ring 300. The distal edge 324 of the locking tab 320 can be even with the distal face 306 of the locking ring 300 or a distance proximally from the distal face 306 of the locking ring 300.

The outside curvature of the ramped face 326 of the at least one locking tab 320 can vary. The ramped face 326 can be a flat surface, a curved surface or any other shaped surface. In some embodiments, the ramped face 326 of the at least one locking tab 320 is curved to be concentric to the hollow cylindrical body 302 of the locking ring 300.

The number of locking tabs 320 can vary depending on, for example, the shape of the hub 200 and outer shield 400. At least one locking tabs 320 is included on the locking ring 300. The embodiment shown in FIGS. 7 and 8 have two locking tabs 320, but it will be understood by those skilled in the art that any number of locking tabs 320 can be incorporated into the locking ring 300. For example, if the hub 200 is an elongate decahedron with ten longitudinal channels 208, then the locking ring 300 can have up to ten locking tabs 320, with each of the locking tabs 320 aligned with a longitudinal groove 208 on the hub 200. In some embodiments, the locking ring 300 includes two locking tabs 320 positioned on opposite sides of the hollow cylindrical body 302. The spacing of the locking tabs 320 about the hollow cylindrical 302 can be distributed in any suitable manner and at any suitable degrees about the locking ring 300. For example, there can be two locking tabs 320 spaced 180° apart, or spaced in the range of about 10° to about 170° apart. In another example there are in the range of two locking tabs 320 to ten locking tabs 320 spaced in the range of about 5° to about 175° apart.

In some embodiments, the locking ring 300 includes two ring elements 310 on opposite sides of the hollow cylindrical body 300 and two locking tabs 320 on opposite sides of the hollow cylindrical body 300 alternating with the ring elements 310.

Figure 12:
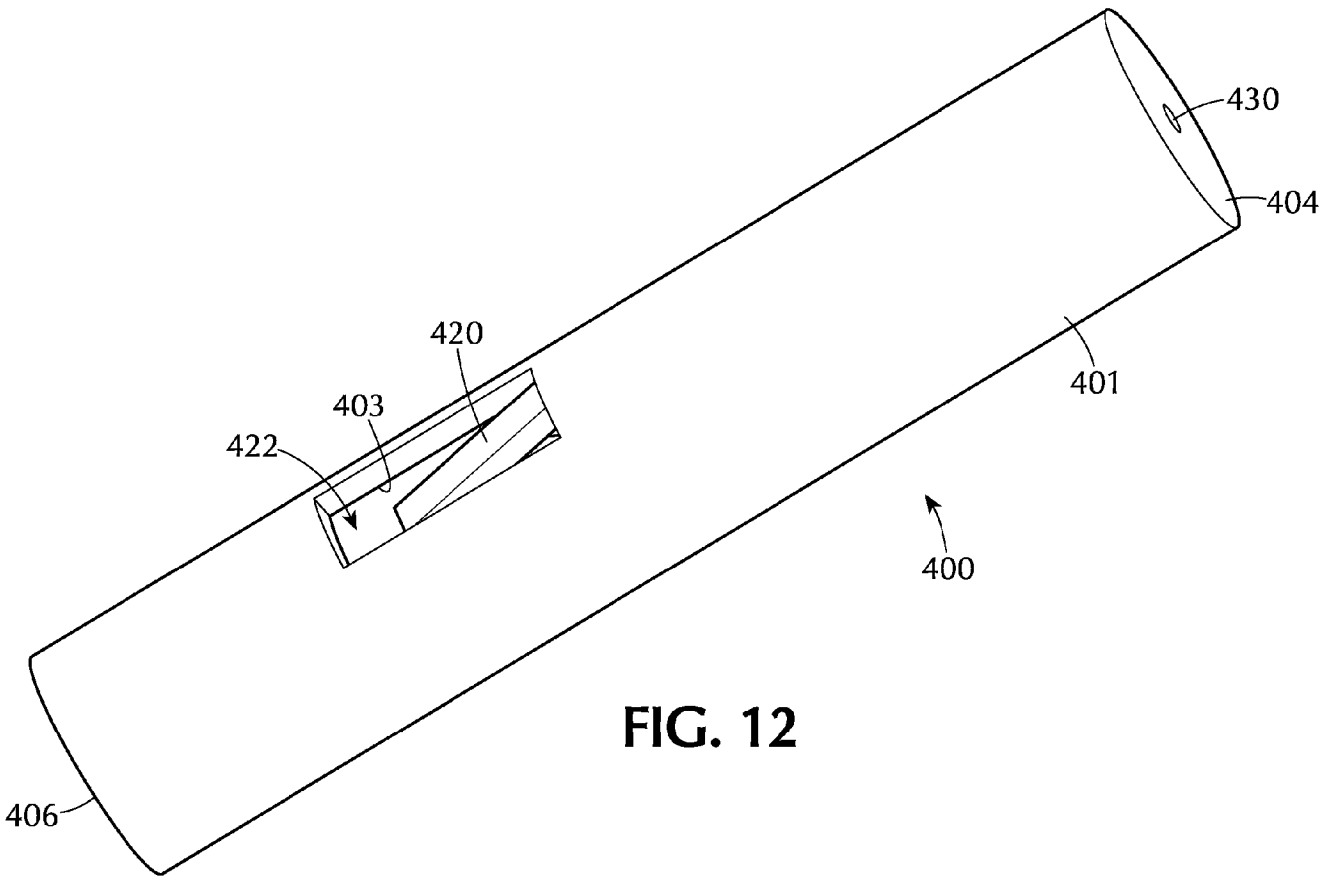
FIG. 12 is an isometric view of an opaque outer shield portion of a safety needle device in accordance with one or more embodiments of the invention.
Figure 13:
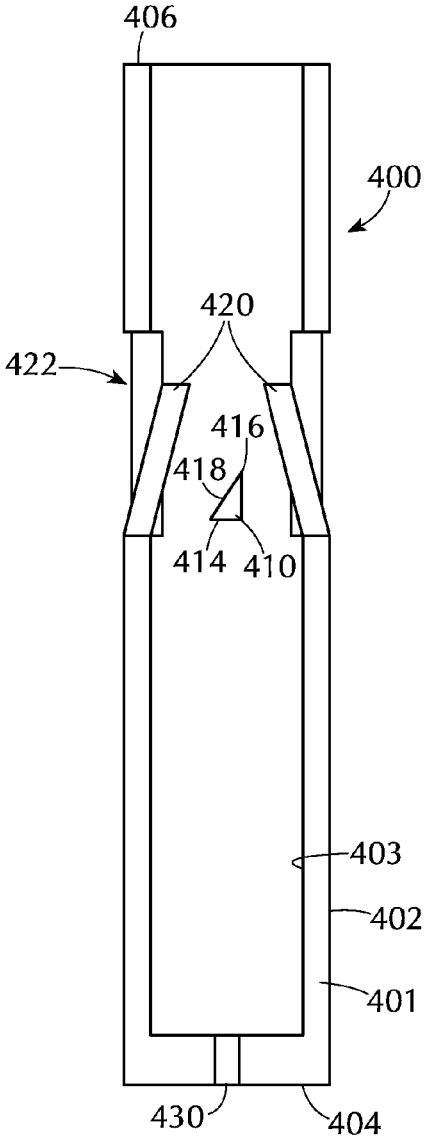
FIG. 13 is a side cross-sectional view of an outer shield portion of a safety needle device in accordance with one or more embodiments of the invention.
Figure 14:
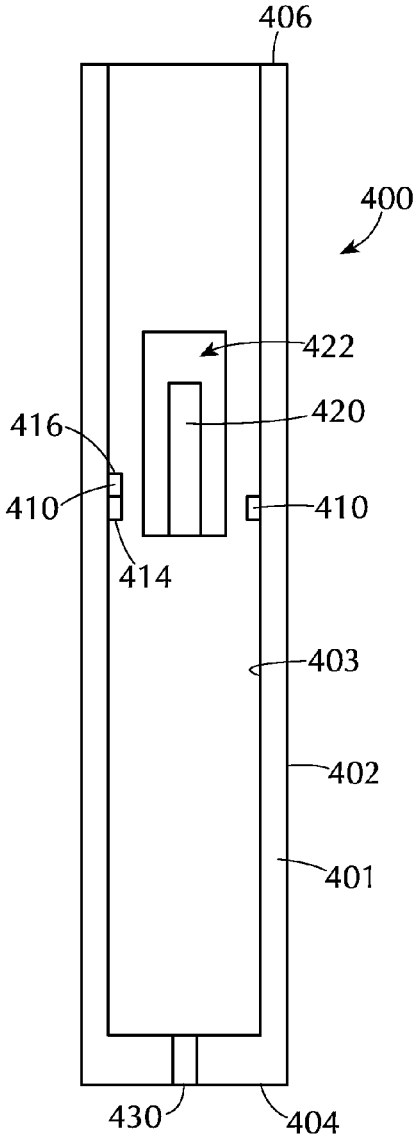
FIG. 14 is a side cross-sectional view of an outer shield of a safety needle device in accordance with one or more embodiments of the invention.

Referring to FIGS. 12-14, the assembly includes an outer shield 400 comprising an elongate, hollow body 401 having a closed proximal end 404, an open distal end 406, an outer surface 402 and an inner surface 403. FIG. 12 shows an isometric view of an opaque outer shield 400. FIGS. 13-14 show cross-sectional view of the outer shield 400 shown in FIG. 12 with the inner features visible.

The outer shield 400 includes at least one activation element 410 protruding inwardly from the inner surface 403. The at least one activation element 410 works cooperatively with the at least one ring element 310 on the locking ring 300. The cooperative interaction between the activation element 410 and the ring element 310 causes rotation of the locking ring 300 within the circumferential channel 212 of the hub.

The at least one activation element 410 can be any suitable shape to interact the ring element 310. In some embodiments, the activation element 410 is a substantially triangular wedge with a proximal end 414 and distal end 416. The proximal end 414 is wider than the distal end 416. A sloped surface 418 extends from the proximal end 414 to the distal end 416.

The number of activation elements 410 can vary depending on, for example, the shape of the outer shield 400 and the hub 200. At least one activation element 410 is included on the outer shield 400. The embodiment shown in FIGS. 13 and 14 have two activation elements 410, but it will be understood by those skilled in the art that any number of activation elements 410 can be incorporated into the outer shield 400. For example, if the outer shield 400 and hub 200 are elongate decahedron with ten longitudinal channels 208, then the outer shield 400 can have up to ten activation elements 410, with each of the activation elements 410 aligned with a longitudinal groove 208 on the hub 200. In some embodiments, the outer shield 400 includes two activation elements 410 positioned on opposite sides of the outer shield 400. The spacing of the activation elements 410 can be distributed in any suitable manner and at any suitable degrees about the outer shield 400. For example, there can be two activation elements 410 spaced 180° apart, or spaced in the range of about 10° to about 170° apart. In another example there are in the range of two activation elements 410 to ten activation elements 410 spaced in the range of about 5° to about 175° apart.

The outer shield also includes at least one finger 420 biased radially inwardly from the body 401. In the embodiments shown in FIGS. 12-14, there are two fingers 420 positioned within an opening 422. The opening 422 is an option component and may provide for increased flexing of the finger 420 distal movement that disables the assembly, as described further below. The fingers 420 can be any suitable shape and are not limited to those shown in the Figures.

The number of fingers 420 can vary depending on, for example, the shape of the outer shield 400 and the hub 200. At least one fingers 420 is included on the outer shield 400. The embodiment shown in FIGS. 13 and 14 have two fingers 420, but it will be understood by those skilled in the art that any number of fingers 420 can be incorporated into the outer shield 400. For example, if the outer shield 400 and hub 200 are elongate decahedron with ten longitudinal channels 208, then the outer shield 400 can have up to ten fingers 420, with each of the fingers 420 aligned with a longitudinal groove 208 on the hub 200. In some embodiments, the outer shield 400 includes two fingers 420 positioned on opposite sides of the outer shield 400. The spacing of the fingers 420 can be distributed in any suitable manner and at any suitable degrees about the outer shield 400. For example, there can be two fingers 420 spaced 180° apart, or spaced in the range of about 10° to about 170° apart. In another example there are in the range of two fingers 420 to ten fingers 420 spaced in the range of about 5° to about 175° apart.

Some embodiment of the outer shield further comprise an aperture 430 on the closed proximal end 404. The aperture 430 can permit a needle or other device to extend therethrough.

Referring back to FIGS. 1 and 2, some embodiments of the assembly include a spring element 500 which causes the outer shield 400 to slide proximally with respect to the hub 200. A spring element 500 is not limited to springs, but is any component with a spring constant capable of causing the desired relative movement. In some embodiments the spring element 500 is a spring which contacts the proximal end 204 of the hub 200 and the inside of the closed proximal end 404 of the outer shield 400. The spring element 500 compresses with manual force to allow the proximal end 204 of the hub 200 to travel slidably with in the outer shield 400 toward the closed proximal end 404 of the outer shield. Suitable spring elements include, but are not limited to, springs, foams, plastic, and rubber components with a suitable spring constant. The spring element 500 can be any suitable shape including, but not limited to helical or leaf shaped elements. Springs in any form or material may be used in addition to compressible solid bodies (i.e. foams) to achieve proximal axial movement of the outer shield relative to the hub.

The assembly further comprises a needle 600. The needle can be positioned to extend from the proximal end 404 of the outer shield 400 or from the distal end 206 of the hub 200 upon compression of the spring element 500. In some embodiments, the needle 600 extends from the proximal end 204 of the hub 200 within the spring element 500 and the outer shield 400 such that proximal movement of the hub 200 with respect to the outer shield 400 compresses the spring element 500 and causes the needle 600 to project through the aperture 430 in the outer shield 400. The needle 600 can be affixed to the proximal end 204 of the hub so that the relative movement of the outer shield 400 with respect to the hub 200 causes the tip 602 of the needle to extend through the aperture 430. The needle 600 is hollow to allow passage of a substance through the needle and can be in fluid communication with the aperture 210 in the hub 200 to allow passage of a fluid through the hub and the needle. In one or more embodiments, the hub further comprises a Luer connector 218 on the proximal end 20. The Luer connector 218 can be a Luer slip or Luer lock connenctor.

In some embodiments, the needle 600 is positioned within the hub 200 so that distal movement of the outer shield 400 with respect to the hub 200 compresses the spring element 500 and causes the needle 600 to extend from the distal end 206 of the hub 200. In embodiments, of the this sort, the needle 500 can be connected to the outer shield 400 so that the needle tip 602 remains a fixed distance the connection point to the outer shield. The needle 600 may be any length suitable for hypodermic injections. The needle 600 is hollow to allow passage of a fluid through the needle. In one or more embodiments, the outer shield 400 further comprises a Luer connector on the proximal end 404 of the outer shield 400.

Figure 15:
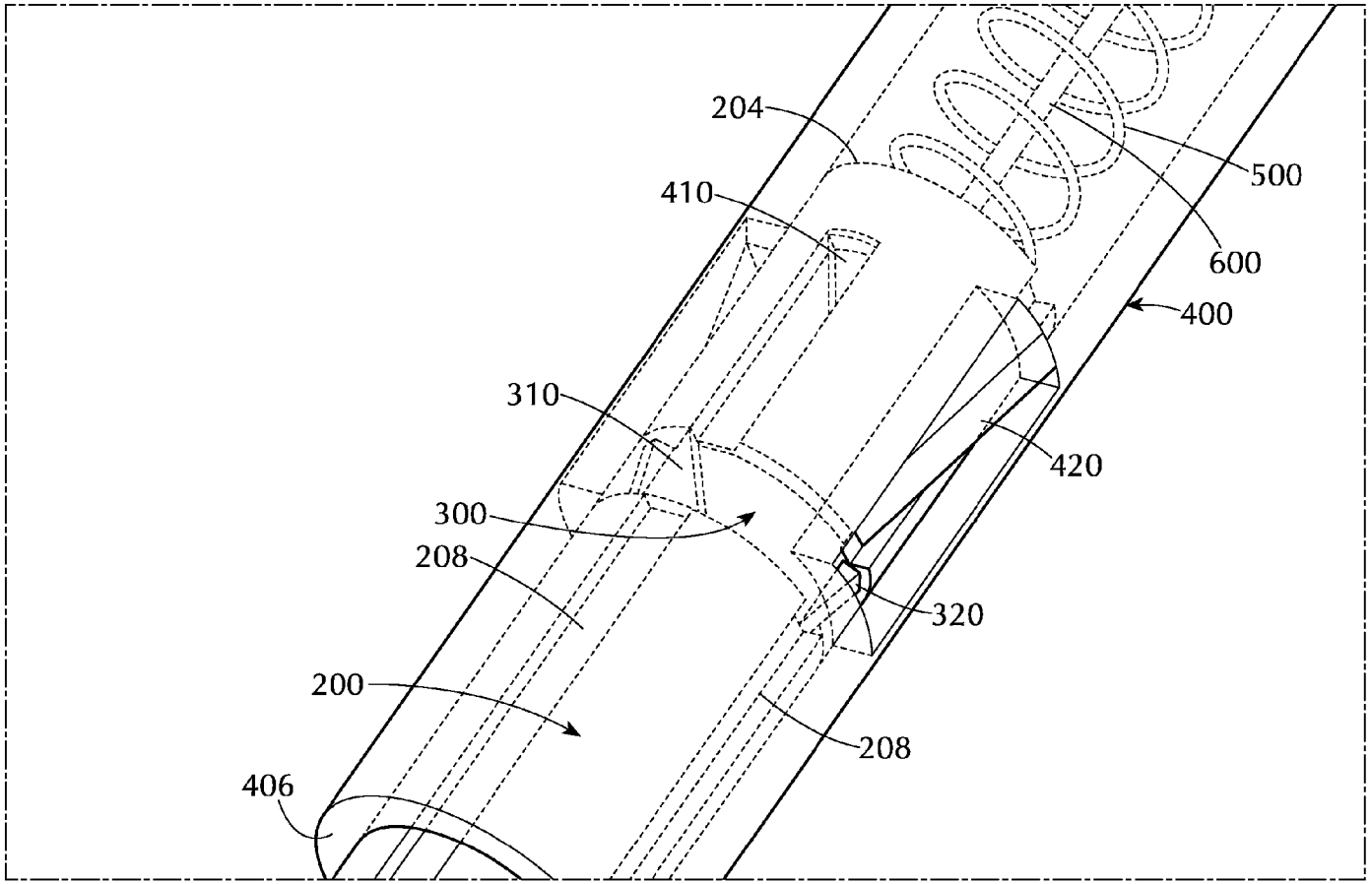
FIG. 15 is a perspective view of a safety needle device in an unlocked state in accordance with one or more embodiments of the invention.

Referring to FIGS. 15-18, the use of the assembly of some embodiments is described. These Figures show expanded views of the proximal end 204 of the hub 200, the distal end 406 of the outer shield 400 and the locking ring 300. FIG. 15 shows the assembly in the unlocked state where distal movement of the outer shield 400 with respect to the hub 200 is possible. It can be seen from FIG. 15 that in this initial state, the ring element 310 is aligned with a longitudinal groove 208 on the hub. The activation element 410 on the outer shield 400 is also aligned within the longitudinal groove 208. The finger 420 is aligned within a second longitudinal groove 208 and the locking tab 320 is not aligned with the longitudinal groove 208. This alignment allows the finger 420 to pass the locking tab 320 without interference.

Figure 16:
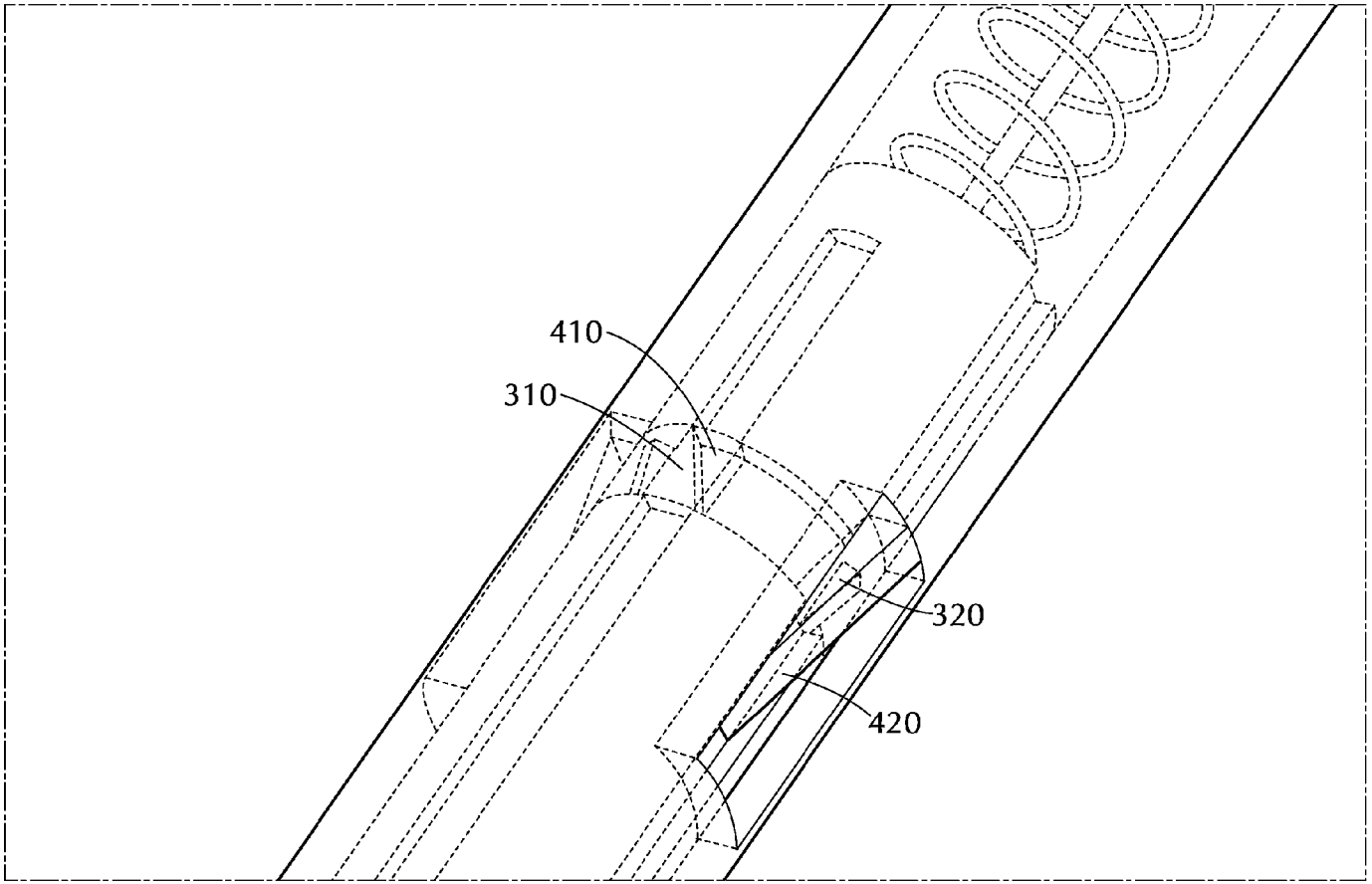
FIG. 16 is a perspective view of the safety needle device of FIG. 15 in the process of locking in accordance with one or more embodiments of the invention.
Figure 17:
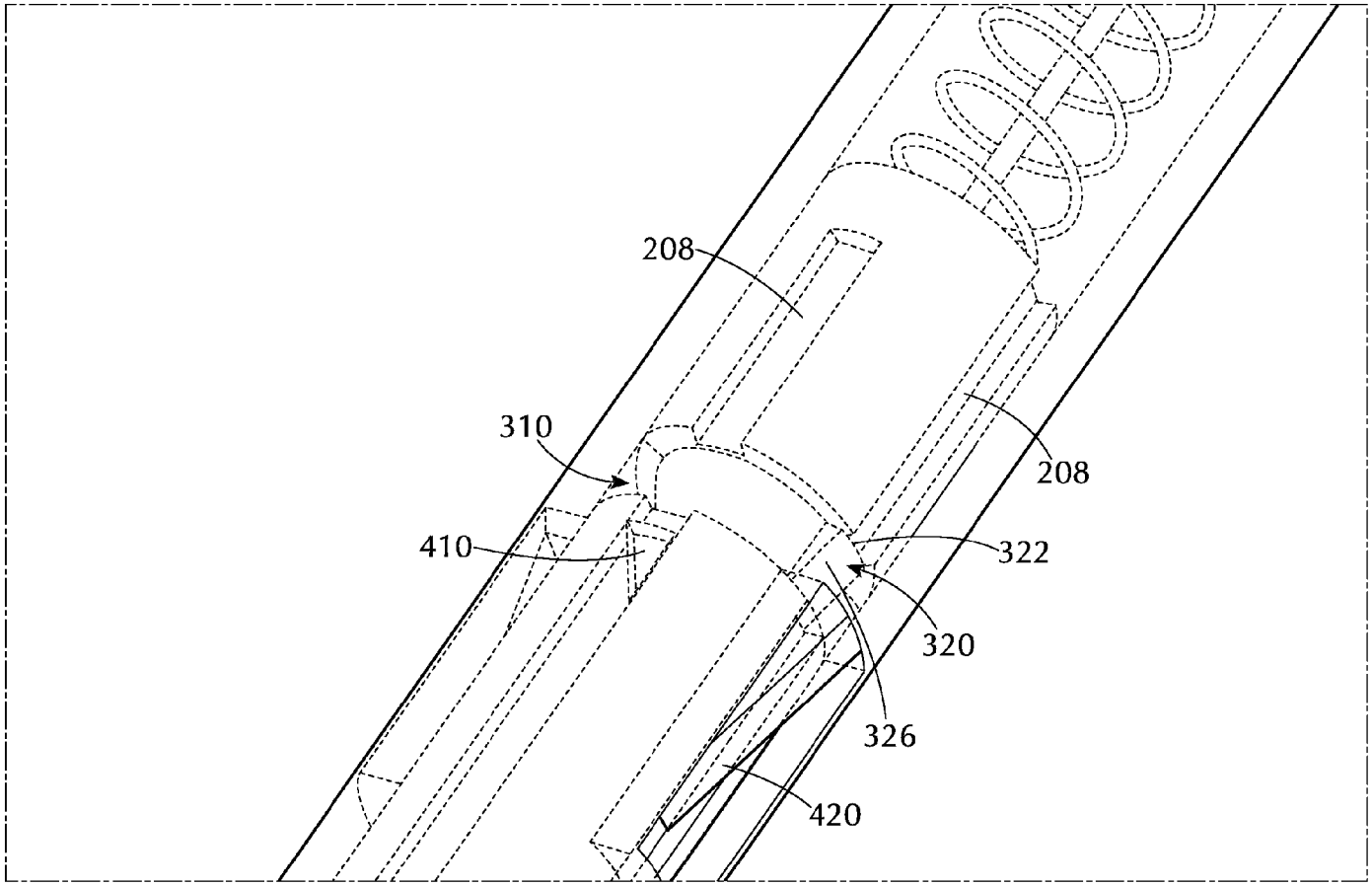
FIG. 17 is a perspective view of the safety needle device of FIG. 16 in the process of locking in accordance with one or more embodiments of the invention.

From this position, the outer shield 400 is moved distally to the point shown in FIG. 16. Here, the activation element 410 has made contact with the ring element 310 and the end of the finger 420 has distally passed the locking ring 300. The spring element 500 has started to become compressed and the needle tip is traveling, relatively, toward either the proximal end of the outer shield 400 or the distal end of the hub 200.

Further distal movement of the outer shield 400 with respect to the hub 200 causes the activation element 410 to apply distally directed and rotation force to the ring element 310. This rotational force causes the locking ring 300 to rotate until the activation element 410 has completely passed the ring element 310. This can be seen in FIG. 17 where the activation element 410 is now located distally of the locking ring. The rotation of the locking ring 300 results in the locking tab 320 being rotated from out of alignment with the finger 420 and longitudinal groove 208, to being aligned with the finger 420 and longitudinal groove 208 so that the ramped surface 326 is in the return path of the finger 420.

Figure 18:
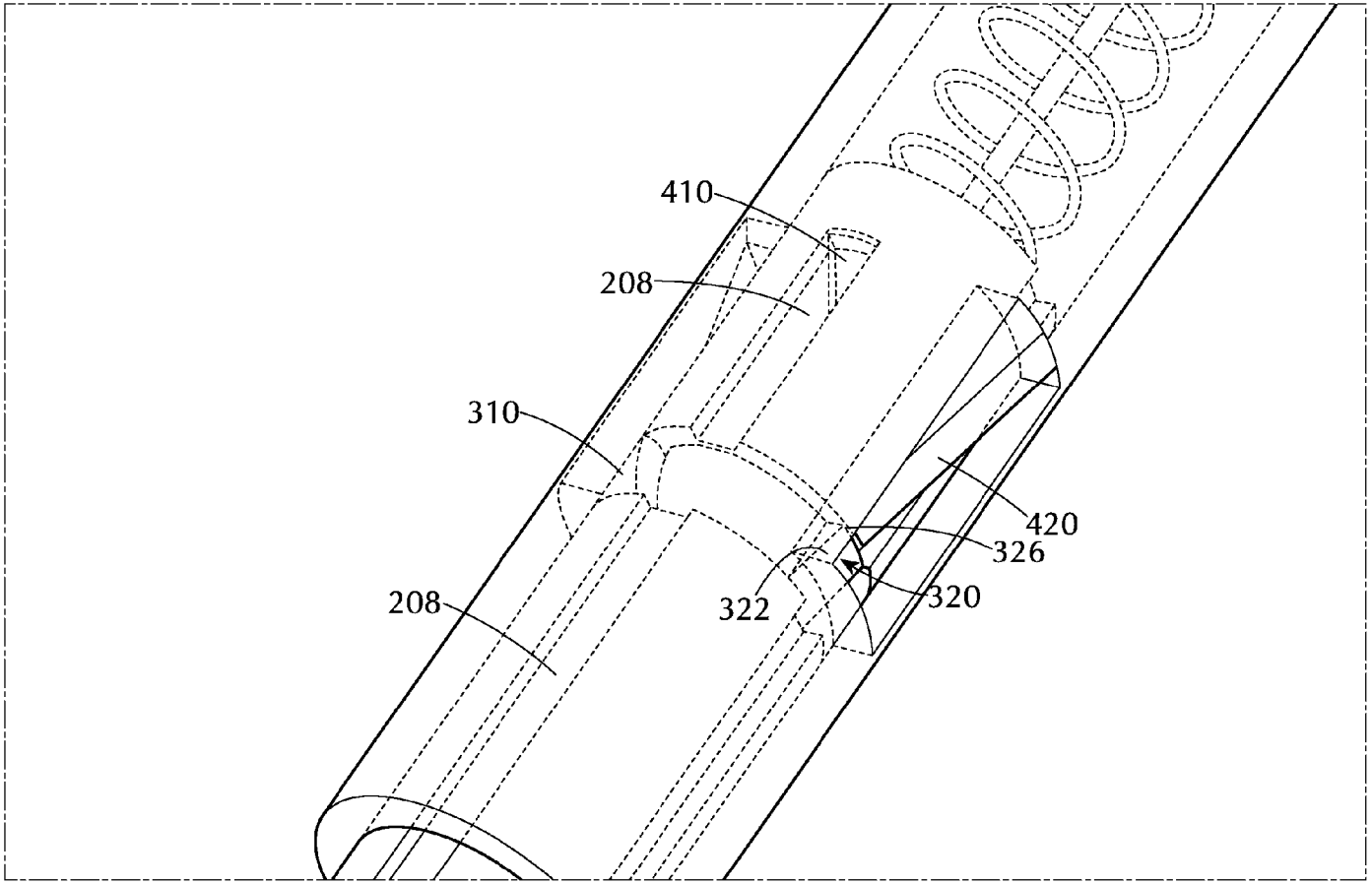
FIG. 18 is a perspective view of the safety needle device of FIG. 17 in the locked state in accordance with one or more embodiments of the invention.
Figure 19:
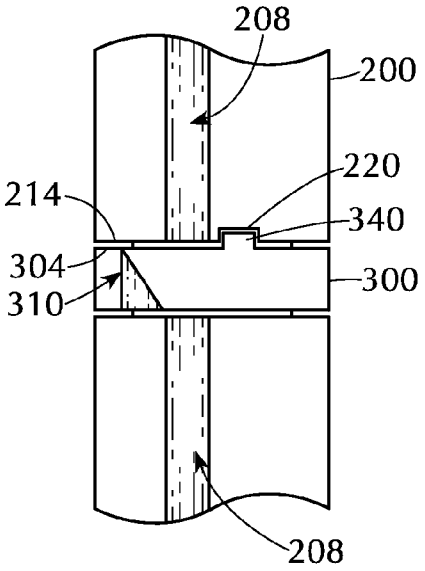
FIG. 19. shows the coordination of a locking ring and hub in accordance with one or more embodiments of the invention.

Cessation of distally directed force on the outer shield 400, or proximal movement of the outer shield 400 with respect to the hub 200 (e.g., after injection) results in a locked assembly. FIG. 18 shows the final locked state of the assembly. The proximal movement of the outer shield 400 causes the at least one finger 420 to ride up the ramped surface 326 and engage the proximal facing edge 326 preventing further relative movement of the outer shield 400 and hub 200. It can be seen from FIG. 18, that further relative movement of the outer shield 400 proximally is prevented by the interaction of the activation element 410 with the end of the longitudinal groove 208. However, this can also be accomplished by the finger 420 becoming entrapped between the proximal facing edge 326 and an end of the longitudinal groove 208.

In some embodiments, the locking ring 300 includes at least one projection 340 from one or more of the proximal face 304 and the distal face 306. The at least one projection 340 can cooperatively interact with at least one complementary recess 220 in the hub 200. In one or more embodiments, the projection 340 extends proximally from the proximal face 304 of the hollow cylindrical body 302. In some embodiments, the projection 340 extends distally from the distal face 306 of the hollow cylindrical body 302. The number of projections 340 can vary depending on a variety of factors.

FIGS. 19-25 show some embodiments of projections 340 and recesses 220 that may be employed. Each of the Figures shows a portion of a hub 200 with a locking ring 300. For clarity, only one ring element 310 is shown on the locking ring 300 and no locking tabs 320 are shown. Additionally, for clarity, a single longitudinal groove 208 is shown for each of the hubs 200. The embodiment shown in FIG. 12 shows a locking ring 300 with a square-shaped projection 340 that is engaged with a square-shaped recess on the hub 200. The ring element 310 is not aligned with the longitudinal groove 208, indicating that the locking ring 300 is in the locked position. The projection 340 extends from the proximal face 304 of the locking ring 300 and is engaged with a recess 220 located on the proximal end 214 of the circumferential channel 212.

Figure 20:
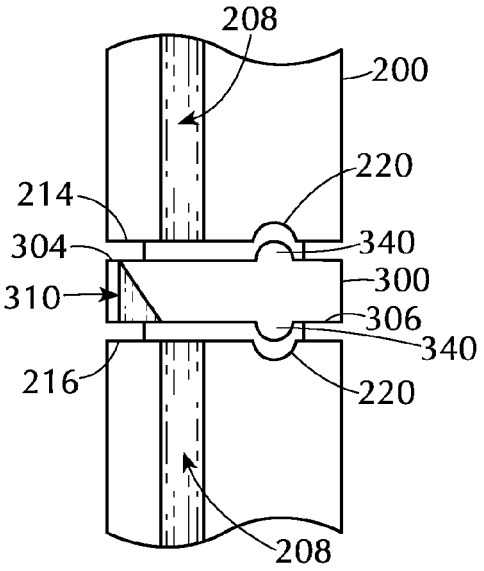
FIG. 20. shows the coordination of a locking ring and hub in accordance with one or more embodiments of the invention.

FIG. 20 shows an embodiment in which there are two arc-shaped projections 220 on the locking ring 300. A first projection 340 extends proximally from the proximal face 304 of the locking ring 300 and is engaged with a first recess 220 located on the proximal end 214 of the circumferential channel 212. A second projection 340 extends distally from the distal face 306 of the locking ring 300 and is engaged with a second recess 220 located on the distal end 216 of the circumferential channel 212. The ring element 310 is shown not aligned with the longitudinal groove 208 indicating that the locking ring 300 is in the locked position. In the unlocked position, the projections 340 are friction fit within the circumferential channel 212 but are not engaged with the recesses 220. Rotation of the locking ring 300 to the locked position moves the ring element 310 to be out of alignment with the longitudinal groove 208 and the projections 340 engage the recesses 220 to prevent, or help prevent, further rotation of the locking ring 300 within the recess.

Figure 21:
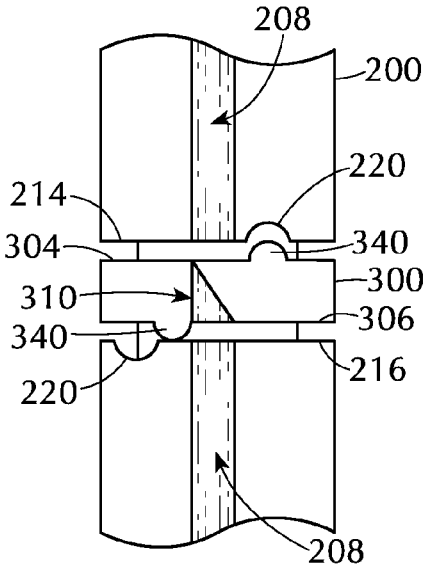
FIG. 21. shows the coordination of a locking ring and hub in accordance with one or more embodiments of the invention.

FIG. 21 shows another embodiment of the locking ring 300 and hub 200 in which there are two projections 340 and two recesses 220. Only one of the projections 340 engage a recess 220 in the unlocked position and only one projection 340 engages a recess 220 when the locking ring 300 is in the locked position. FIG. 21 shows the locking ring 300 in the unlocked position because the ring element 310 is aligned with the longitudinal groove 208. Embodiments of this sort help prevent the locking ring 300 from spontaneous rotation because there is a projection/recess interaction in both the unlocked and locked positions.

The shape of the projection 340 and recess 220 can be any suitable shape including, but not limited to, square, rectangular, trapezoidal, triangular, arc-shaped and finger-like. The embodiment shown in FIG. 19 has a rectangular projection 340 and a matching rectangular recess 220. The embodiment shown in FIGS. 20-21 have arc-shaped projections 340 and arc-shaped recesses 220. It will be understood that the shape of the projection 340 does not need to be the same as the shape of the recess 220 so long as the projections 340 and recess 220 can act cooperatively to mitigate the chance of spontaneous rotation of the locking ring 300.

Figure 22:
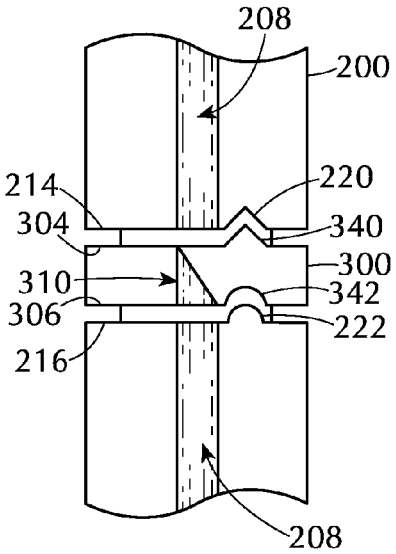
FIG. 22. shows the coordination of a locking ring and hub in accordance with one or more embodiments of the invention.

FIG. 22 shows another embodiment of the locking ring 300 and hub 200 in which there is one projection 340 on the proximal face 304 of the locking ring 300 in a triangle shape with a matching recess 220 on the proximal end 214 of the circumferential channel 212. This embodiment shows an alternate projection and recess combination. A projection 222 on the distal end 216 of the circumferential channel 212 cooperates with a recess 342 on the locking ring 300.

Figure 23:
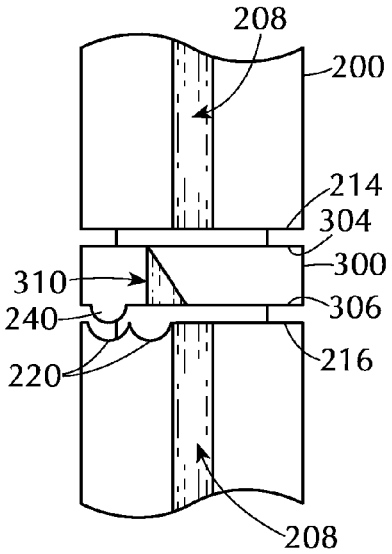
FIG. 23. shows the coordination of a locking ring and hub in accordance with one or more embodiments of the invention.

FIG. 23 shows an embodiment of the locking ring 300 and hub 200 in which there is one projection 340 on the distal face of the locking ring 300 and two recesses 220 on the distal end 216 of the circumferential channel 212. The Figure shows the locking ring 300 in the locked position with the ring element 310 not aligned with the longitudinal groove 208.

Figure 24:
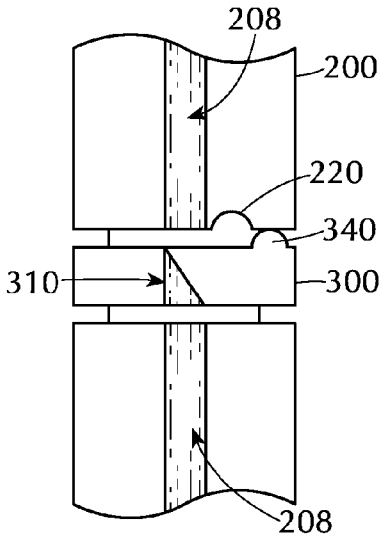
FIG. 24. shows the coordination of a locking ring and hub in accordance with one or more embodiments of the invention.
Figure 25:
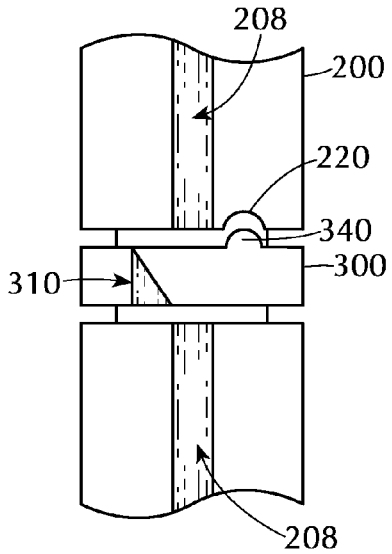
FIG. 25. shows the coordination of a locking ring and hub in accordance with one or more embodiments of the invention.

FIGS. 24-25 show a single embodiment in the unlocked and locked positions. In FIG. 24, the locking ring 300 is in the unlocked position with the ring element 340 in alignment with the longitudinal groove 208. The locking ring 300 and projection 340 are friction fit within the circumferential channel 300 so that there is a decreased possibility of spontaneous rotation. Upon activation of the ring element 310, the ring rotates toward the left so that the ring element 310 is no longer aligned with the longitudinal groove 208 and the projection 340 engages the recess 220 to reach the locked position with the projection 340 in the recess 220 as shown in FIG. 25.

Referring back to FIGS. 7 and 8, some embodiments of the locking ring 300 includes an opening 350 extending from the proximal face 304 to the distal face 306 and through the thickness of the hollow cylindrical body 302. In one or more embodiments, the opening 350 is wider at the outside surface 308 than at the inside surface 307. In some embodiments, at least one projection 340 is posited to extend one or more of proximally form the proximal face 304 or distally from the distal face 306 adjacent the opening 350. In one or more embodiments, there is a recess on the locking ring 300 adjacent the opening 350.

Each component of the assembly can be made from any suitable materials. For example, the components can be plastic, glass, metal and rubber. The needle can be any suitable device and is not strictly limited to needles. Suitable needs include, but are not limited to, stainless steel needles, metallic needles, plastic needles and glass needles. The spring element can be made from any suitable materials and is not limited to springs. The spring element can also be any suitable shape including, but not limited to helical, coiled and leaf shapes. Some embodiments, one or more of the hub 200, locking ring 300, outer shield 400, spring element 500 and needle 600 are made from a material comprising polypropylene. The components can be made from transparent, translucent or opaque materials. In some embodiments, the outer shield 400 is made from a transparent material so that the needle can be observed throughout use.

Reference throughout this specification to "one embodiment," "certain embodiments," "one or more embodiments" or "an embodiment" means that a particular feature, structure, material, or characteristic described in connection with the embodiment is included in at least one embodiment of the invention. Thus, the appearances of the phrases such as "in one or more embodiments," "in certain embodiments," "in one embodiment" or "in an embodiment" in various places throughout this specification are not necessarily referring to the same embodiment of the invention. Furthermore, the particular features, structures, materials, or characteristics may be combined in any suitable manner in one or more embodiments.

Although the invention herein has been described with reference to particular embodiments, it is to be understood that these embodiments are merely illustrative of the principles and applications of the present invention. It will be apparent to those skilled in the art that various modifications and variations can be made to the method and apparatus of the present invention without departing from the spirit and scope of the invention. Thus, it is intended that the present invention include modifications and variations that are within the scope of the appended claims and their equivalents.

What is claimed is:

[1. A passively activated safety needle assembly comprising:

a hub having an elongate cylindrical body with an outer surface, a distal end and a proximal end defining a length, an aperture extending through the length of the hub, at least two longitudinal grooves extending at least partially along the length of the hub, and a circumferential channel;

a locking ring having a cylindrical body rotatably positioned in the circumferential channel and coaxial with the hub, the locking ring including at least one ring element extending outwardly from an outside surface of the locking ring, the at least one ring element having a proximal end, a distal end and a ramped face extending from the proximal end to the distal end, and at least one ramp-shaped locking tab extending outwardly from the outside surface of the locking ring, the at least one locking tab having a proximal locking face extending from the outside surface of the cylindrical body;

an outer shield coaxial to and slidable around the hub and locking ring, the outer shield including an elongate hollow cylindrical body with an open distal end and a closed proximal end with an aperture to permit a needle to move therethrough, at least one activation element projecting inwardly from an interior surface of the outer shield that engages the at least one ring element, the at least one activation element sized to slidably move within a longitudinal groove on the hub and having a shape that cooperatively interacts with the at least one ring element on the locking ring, and at least one finger projecting inwardly from the outer shield and sized to slidably move within a longitudinal groove on the hub;

a spring element positioned adjacent the proximal end of the hub within the outer shield; and a needle extending from the proximal end of the hub within the outer shield and the spring element, wherein proximally directed force on the hub causes compression of the spring element, extends a tip of the needle through the aperture in the outer shield, and causes the activation element to exert distally directed force onto the ring element to rotate the locking ring such that the at least one finger on the outer shield aligns with the at least one ramped surface.]

[2. The assembly of claim 1, wherein subsequent release of the proximally directed force allows the spring element to expand causing distal movement of the hub with respect to the outer shield so that the at least one finger slides over the at least one ramped surface and that additional proximal movement of the hub is prevented by interaction of the at least one finger with the proximal locking face.]

[3. A passively activated safety needle assembly comprising:

an elongate, hollow outer shield having a distal end, a proximal end, an outer surface and an inner surface, an activation element protruding inwardly from the inner surface, and at least one finger biased radially inwardly;

an elongate hub having a distal end and a proximal end, the hub slidably engaged with the outer shield and biased to move in proximal direction, the hub including a longitudinal groove that guides the activation element during relative sliding motion between the hub and the outer shield;

a spring element positioned within the elongate, hollow outer shield adjacent the proximal end of the elongate hub a locking ring on the hub having a ring element complementary to the activation element and at least one ramped surface radially spaced from the ring element and providing a proximal facing edge, wherein distal movement of the outer shield with respect to the hub causes the activation element and ring element to rotate the locking ring such that the at least one finger aligns with the ramped surface and subsequent proximal movement of the outer shield causes the at least one finger to engage the proximal facing edge, preventing further relative movement of the outer shield and hub.]

[4. The assembly of claim 3, wherein the hub includes a circumferential channel and the locking ring is rotatably seated within the circumferential channel.]

[5. The assembly of claim 3, wherein the ring element is a substantially triangular wedge with a proximal end and a distal end, the proximal end being narrower than the distal end.]

[6. The assembly of claim 3, wherein the activation element is a substantially triangular wedge with a proximal end and distal end, the proximal end being wider than the distal end.]

[7. The assembly of claim 3, wherein there are two activation elements.]

[8. The assembly of claim 3, wherein the locking ring further comprises a longitudinal opening.]

[9. The assembly of claim 3, further comprising a needle positioned within the hub so that distal movement of the outer shield with respect to the hub compresses the spring element and causes the needle to extend from the distal end of the hub.]

[10. The assembly of claim 3, wherein the activation element is a substantially triangular wedge with a proximal end and distal end narrower than the proximal end and the ring element if a complementary triangular wedge with a proximal end and distal end wider than the proximal end.]

[11. The assembly of claim 10, wherein the activation elements are positioned on opposite sides of the outer shield.]

[12. The assembly of claim 3, wherein there are two ring elements.]

[13. The assembly of claim 12, wherein the ring elements are on opposite sides of the locking ring.]

[14. The assembly of claim 3, wherein the locking ring further comprises a projection extending one or more of proximally and distally from the locking ring.]

[15. The assembly of claim 14, wherein the elongate hub further comprises at least one complementary recess that engages the projection.]

[16. The assembly of claim 3, wherein the elongate, hollow outer shield further comprises an aperture that permits a needle to extend therethrough.]

[17. The assembly of claim 16, further comprising a needle extending from the proximal end of the elongate hub within the spring element and the outer shield such that proximal movement of the hub with respect to the outer shield compresses the spring element and causes the needle to project through the aperture.]

[18. The assembly of claim 17, wherein the needle is connected to the elongate hub using a Luer connector on the proximal end of the elongate hub.]

*19. A safety needle assembly comprising:*

*an elongate cylindrical body having an outer surface, an inner surface, and a length, an aperture extending through the length of the elongate cylindrical body and a longitudinal groove extending at least partially along the length of the elongate cylindrical body;*

*a ring-based component having a hollow cylindrical body positioned and coaxial with respect to the elongate cylindrical body;*

*an outer shield coaxial to and slidable with respect to the elongate cylindrical body and the ring-based component, the outer shield including an elongate hollow cylindrical body with an open end to permit a needle to move therethrough;*

*the outer shield having an activation element that engages the ring-based component;*

*a spring element positioned within the outer shield; and*

*a needle extending within the outer shield and the spring element, the needle having a tip, wherein an axially-directed force causes compression of the spring element, causing the outer shield to travel freely, and subsequent release of the axially-directed force allows the spring element to expand, causing the outer shield to retract, providing protection against needle stick injuries, and wherein the axially directed force causes the ring-based component and the outer shield to rotate with respect to each other, the ring-based component has a ring element, wherein the activation element and the ring element engage each other, the ring element extends outwardly from the ring-based component, and the ring element has a ramped surface that can transfer axially directed force into rotational force and wherein the ring-based component further comprises an outwardly extending tab which moves in the longitudinal groove upon axial movement of the outer shield.*

*20. The safety needle assembly of claim 19, wherein the activation element has a shape and the ring element has a shape such that the activation element and the ring element work cooperatively.*

*21. The safety needle assembly of claim 20, wherein the elongate cylindrical body has a channel, and the ring-based component fits within the channel.*

*22. The safety needle assembly of claim 19, wherein the ring element is peg-shaped.*

*23. The safety needle assembly of claim 19, wherein axial movement of the outer shield with respect to the elongate cylindrical body causes the activation element and the ring element to engage.*

*24. The safety needle assembly of claim 19, wherein cessation of axially directed force on the outer shield results in the assembly being locked.*

*25. The safety needle assembly of claim 24, wherein cessation of axially directed force on the outer shield prevents further relative movement of the outer shield and the elongate cylindrical body.*

*26. A safety needle assembly comprising:*

*an elongate cylindrical body having an outer surface, an inner surface, and a length, an aperture extending through the length of the elongate cylindrical body and at least two longitudinal grooves extending at least partially along the length of the elongate cylindrical body;*

*a hollow cylindrical body positioned and coaxial with respect to the elongate cylindrical body;*

*an outer shield coaxial to and slidable with respect to the elongate cylindrical body and the hollow cylindrical body, the outer shield including an elongate hollow cylindrical body with an open end to permit a needle to move therethrough;*

*the outer shield having an activation element that engages the hollow cylindrical body;*

*a spring element positioned within the outer shield;*

*and a ring-based component having a ring element, wherein the ring element extends outwardly from the hollow cylindrical body and the ring element has ramped surface that transfers axially directed force into rotational force, wherein the outwardly extending tab moves in one of the at least two longitudinal grooves upon axial movement of the outer shield; and*

*a needle extending within the outer shield and the spring element, the needle having a tip, wherein an axially-directed force causes compression of the spring element, causing the outer shield to travel freely, and subsequent cessation of the axially-directed force allows the spring element to expand, causing the outer shield to retract, resulting in the assembly being locked.*

*27. The safety needle assembly of claim 26, wherein cessation of axially directed force on the outer shield prevents further relative movement of the outer shield and the elongate cylindrical body.*

*28. The safety needle assembly of claim 26, the outer shield further comprising an activation element and the hollow cylindrical body, wherein the activation element and the ring element can engage each other.*

*29. The safety needle assembly of claim 26, wherein the ring element is peg-shaped.*

*30. The safety needle assembly of claim 29, wherein the hollow cylindrical body further comprises an outwardly extending tab.*

*31. The safety needle assembly of claim 30, wherein the outwardly extending tab can move in one of the at least two longitudinal grooves upon axial movement of the outer shield.*

* * * * *